(12) United States Patent
Moller et al.

(10) Patent No.: US 10,159,687 B2
(45) Date of Patent: Dec. 25, 2018

(54) PRODRUGS OF VITAMIN K

(71) Applicant: KAPPA BIOSCIENCE AS, Oslo (NO)

(72) Inventors: Mona Moller, Oslo (NO); Marcel Sandberg, Oslo (NO); Inger Reidun Aukrust, Oslo (NO)

(73) Assignee: KAPPA BIOSCIENCE AS, Oslo (NO)

( * ) Notice: Subject to any disclaimer, the term of this patent is extended or adjusted under 35 U.S.C. 154(b) by 0 days.

(21) Appl. No.: 15/369,060

(22) Filed: Dec. 5, 2016

(65) Prior Publication Data
US 2017/0079994 A1 Mar. 23, 2017

Related U.S. Application Data

(62) Division of application No. 14/382,225, filed as application No. PCT/EP2013/054298 on Mar. 4, 2013, now Pat. No. 9,512,153.

(30) Foreign Application Priority Data

Mar. 2, 2012 (GB) .................................. 1203705.7

(51) Int. Cl.
| | | |
|---|---|---|
| A61K 31/661 | (2006.01) | |
| A61K 31/222 | (2006.01) | |
| A61K 31/235 | (2006.01) | |
| C07C 69/78 | (2006.01) | |
| C07C 69/76 | (2006.01) | |
| C07C 69/34 | (2006.01) | |
| C07C 69/017 | (2006.01) | |
| C07F 9/09 | (2006.01) | |
| C07C 69/16 | (2006.01) | |
| C07C 69/28 | (2006.01) | |
| C07C 69/40 | (2006.01) | |
| C07F 9/12 | (2006.01) | |
| C07C 271/22 | (2006.01) | |
| A61K 31/325 | (2006.01) | |

(52) U.S. Cl.
CPC .......... *A61K 31/661* (2013.01); *A61K 31/222* (2013.01); *A61K 31/235* (2013.01); *A61K 31/325* (2013.01); *C07C 69/017* (2013.01); *C07C 69/16* (2013.01); *C07C 69/28* (2013.01); *C07C 69/34* (2013.01); *C07C 69/40* (2013.01); *C07C 69/76* (2013.01); *C07C 69/78* (2013.01); *C07C 271/22* (2013.01); *C07F 9/098* (2013.01); *C07F 9/12* (2013.01)

(58) Field of Classification Search
CPC ...... A61K 31/325; C07C 69/16; C07C 69/34; C07C 69/40; C07C 69/78
See application file for complete search history.

(56) References Cited

U.S. PATENT DOCUMENTS

| | | | |
|---|---|---|---|
| 2,456,686 A | 12/1948 | Doisy et al. | |
| 3,127,434 A | 3/1964 | Maynard | |
| 6,746,678 B1 * | 6/2004 | Shapiro ................. | A61K 31/18 424/400 |
| 2005/0090553 A1 | 4/2005 | Shapiro | |
| 2008/0220094 A1 | 9/2008 | Bobyock et al. | |
| 2008/0234380 A1 | 9/2008 | Shapiro | |

FOREIGN PATENT DOCUMENTS

| | | |
|---|---|---|
| CN | 103142568 A | 6/2013 |
| DE | 19964116 A1 | 7/2001 |
| EP | 0679394 A2 | 11/1995 |
| EP | 2060256 A1 | 5/2009 |
| GB | 893172 A | 4/1962 |
| GB | 1424004 A | 2/1976 |
| GB | 1426769 A | 3/1976 |
| JP | H1035256 A | 2/1998 |
| JP | WO2006080463 A1 * | 8/2006 |
| WO | 2010/034999 A1 | 4/2010 |
| WO | 2010035000 A1 | 4/2010 |
| WO | 2011152810 A1 | 12/2011 |
| WO | 2012161572 A1 | 11/2012 |
| WO | 2013128037 A1 | 9/2013 |

OTHER PUBLICATIONS

Wikipedia, Wikipedia, Vitamin K2, Aug. 2017, pp. 1-8, recovered from https:/en.wikipedia.org/wiki/Vitamin_K2 on Oct. 11, 2017 (Year: 2017).*
Jun. 11, 2013 (WO) International Search Report—App PCT/EP2013/054298.
Jun. 20, 2011—(GB) Search Report—App 1103549.0.
Isler et al: Helvetica Chimica Acta, vol. 41, 1958, pp. 786-807, ISSN: 0018-019X, see Chem. Abs. No. 53:11722.
Andrews: Synthesis of Quinol Monophosphates from Vitamin K, 1961, 1808-1816.
Fieser et al: Vitamin K Activity and structure, 659-692, 1940.
Sato et al., Journal of the Chemical Society, Perkin Transactions 1: Organic and Bio-Organic Chemistry (1972-1999), vol. 20, 1973, pp. 2289-2293, ISSN: 0300-922X, see Chem. Abs. No. 80:108227.
Buu-hoi et al: Croatica Chemica Acta, vol. 29, 1957, pp. 291-295, ISSN: 0011-1643, see Chem Abs. No. 53:11721.
Noll et al: Helvetica Chimica Acta, vol. 43, 1960, pp. 433-438, ISSN: 0018-019X, see Chem. Abs. No. 55:76297.
Weichet et al., Collection of Czechoslovak Chemical Communications, vol. 25, 1960, pp. 1914-1921, ISSN: 0010-0765, see Chem. Abs. No. 54:128677.
Mukai, et al.: Bulletin of the Chemical Society of Japan, vol. 33, 1960, pp. 453-456, ISSN: 0009-2673, see Chem. Abs. No. 54:128678.
Takata et al: "Prodrug for Bioreductive Activation-Independent Delivery of Menahydroquinone-4: Human Liver Enzymatic Activation and Its Action in Warfarin-Poisoned Human Liver" Biol. Pharm. Bull. (1999) vol. 22, No. 2, pp. 172-178.

(Continued)

*Primary Examiner* — Paul A Zucker
(74) *Attorney, Agent, or Firm* — Banner & Witcoff, Ltd.

(57) ABSTRACT

The disclosure relates to prodrugs of vitamin K2, in particular prodrugs of MK-7 in which the diketone is converted to a monosubstituted or disubstituted ester type derivative. These compounds are shown to give MK-7 in plasma. The disclosure also relates to methods of treating conditions using prodrugs of vitamin K2.

4 Claims, No Drawings

(56) References Cited

OTHER PUBLICATIONS

Zhang et al., Food Biochemistry, China Light Industry Press, p. 120, Aug. 2009.
Shibayama-Imazu et al, Vitamin K2-mediated apoptosis in cancer cells: role of metochondrial transmembrane potential, Vitam Horm, 2008, 78:211-26. doi: 10.1016/S0083-6729(07)00010-6, https:/www.ncbi.nlm.nih.gov/pubmed/18374196.
Choi et al, Vitamin K2 Supplementation Improves Insulin Sensitivity via Osteocalcin Metabolism: a Placebo-Controlled Trial, Diabetes Care, Sep. 2011. 34(9): e147, https://www.ncbi.nlm.nig.gov/pmn/articles/PMC3161300.
Iwamoto et al, Effects of Vitamin K2 on Osteoporosis, Current Pharmaceutical Design, vol. 10, Issue 21, 2004, htttps://doi/org/10.2174/1381612043383782.
Oury et al, Endoctrine regulation of male fertility by the skeleton, Cell, Mar. 4, 2011; 144(5): 796-809, doi:10.1016/j.cell.2011.02.0004, NIH-OA Author Manuscript.
State Pharmaceutical Administration, "Pharmaceutical Chemistry," Chinese Medical Science and Technology Press, p. 203, published May 31, 1996.
Takata et al., Vitamin K prodrugs: 2. Water-Soluble Prodrugs of Menahydroquinone-4 for Systemic Site-Specific Delivery, Pharm Res. Dec. 1995; 12(12):1973-9, Abstract only, 4 pages.
Takata et al., Vitamin K Prodrugs: 1. Synthesis of Amino Acid Esters of Menahydroquinone-4 and Enzymatic Reconversion to an Active Form, Pharmaceutical Research, vol. 12, No. 1, pp. 18-23, 1995.
Suhara et al., Bioorganic & Medicinal Chemistry Letters 2007, 17, pp. 1622-1625.
Tso et al., A Convenient One-flask Synthesis of Vitamin K, J. Chem Research, 1995, pp. 104-105.
Naruta, J. Organic Chemistry, 1980, 45, pp. 4097-4104.
Sep. 30, 2014—(WO) International Search Report and Written Opinion—App PCT/EP20141066886.

\* cited by examiner

PRODRUGS OF VITAMIN K

CROSS-REFERENCE TO RELATED APPLICATIONS

The present application is a divisional of U.S. patent application Ser. No. 14/382,225, filed on Aug. 29, 2014 and issued as U.S. Pat. No. 9,512,152 on Dec. 6, 2016, which is a U.S. National Phase filing of International Application No. PCT/EP2013/054298, filed on Mar. 4, 2013, designating the United States of America and claiming priority to British Patent Application No. 1203705.7, filed Mar. 2, 2012, and this application claims priority to and the benefit of the above-identified applications, which are incorporated by reference herein in their entireties.

TECHNICAL FIELD

This application relates to new prodrugs of vitamin K2 as well as a process for the synthesis of these prodrugs. These prodrugs can be used as nutraceuticals, e.g. for the fortication of foods or simply in supplements or can be used in pharmaceuticals for the treatment of a variety of conditions known to benefit from the administration of vitamin K2.

Vitamin K denotes a group of lipophilic and hydrophobic vitamins that are needed for the post-translational modification of certain proteins, mostly required for blood coagulation. Chemically they are 2-methyl-1,4-naphthoquinone derivatives.

Vitamin K is not a single compound, rather it is a series of related homologues. Vitamin K1 is called phylloquinone and has the systematic name all-E-2-methyl-3-(3,7,11,15-tetramethylhexadec-2-enyl)naphthalene-1,4-dione. Vitamin K2 is a mixture of different molecules based on a naphthoquinone structure and varying lengths of isoprenoid chains. The compound MK-7 (i.e. 7 isoprenyl groups) is depicted below but other components of the vitamin have different numbers of isoprenoid links. Menaquinones have side chains composed of all-E polyprenyl residues; generally they are designated as MK-n, where n specifies the number of isoprenoid repeating units. The minimum value of n is 2.

Whilst vitamin K2 occurs naturally in low concentrations in various fermented food products such as cheese and can to a small extent be produced by bacteria in the intestines, its use as a dietary supplement may be beneficial for many populations. Vitamin K2 can be produced by fermentation of soy beans, but it is still an interesting synthetic target as isolation of the vitamin from a natural source is complex and concentrations of the vitamin are low. Moreover, synthesis allows the preparation of particular menaquinones rather than the isolation of a mixture of different menaquinones.

Various individuals have synthesized the menaquinone compounds which form part of vitamin K2 or components thereof. The first synthesis of menaquinones, reported by Isler et al., Helv. Chim Acta 1958, 41, 786-807, used a nonstereospecific approach. Tso and Chen, J Chem Res 1995, 104-105 describes a one pot synthesis of vitamin K although he concentrates on the formation of the naphthoquinone ring as opposed to the side chain of the molecule. His chemistry involves the reaction of 3-substituted isobenzofuranones with vinylic sulphones to form the naphthoquinone ring structure.

Suhara et al, Bioorg Med Chem Lett 17, (2007) 1622-1625, describe various syntheses of menaquinone analogues in which the terminal methyl group is converted to a hydroxyl, aldehyde or acid group.

Naruta, J Org Chem 1980, 45, 4097-4104, describes the synthesis of some vitamin K2 analogues using trialkylallylstannane chemistry to bond the preformed side-chain to the naphthoquinone group.

The present inventors have previously devised a synthetic strategy for the formation of MK-7 and other menaquinones involving the synthesis of a key intermediate in the manufacturing process (WO2010/035000). This process enables the formation of large synthetic quantities of vitamin K2 not previously enabled in the prior art.

The inventors have realised however, that vitamin K2 is not stable towards oxygen and light. Compositions containing vitamin K2 degrade. Racemisation of the double bonds in the isoprenoid chain leads to an inactive vitamin K2 analogue and these double bonds are obviously susceptible to oxidation. Also, the diketone itself is susceptible to oxidation.

The inventors have realised that useful prodrugs of vitamin K2 can be prepared from mono or disubstituted derivatives of vitamin K2, e.g. mono or diester derivatives, where the ketone functionalities of the naphthoquinone ring are protected. The mono or disubstituted vitamin K2 analogues are capable of undergoing hydrolysis and oxidation in the body to release the equivalent menaquinone type structure. Moreover, the mono or disubstituted compounds are more stable than the vitamin itself in solution and therefore have a longer shelf life. It is even envisaged that these compounds might also improve the bioavailability of the active component. As the nature of the substituents on the certain example compounds maybe tailored, perhaps to include polar functionalities, the solubility profile of the compounds can be manipulated. By making the molecules more soluble than the equivalent menaquinone, it is envisaged that the bioavailability of the vitamin K2 might improve.

Also, certain example compounds may provide a sustained dose of the vitamin K2 compound allowing the production of a "once a day" type product. As the prodrug degrades over time to give the corresponding MK-n compound, a sustained release type formulation is possible.

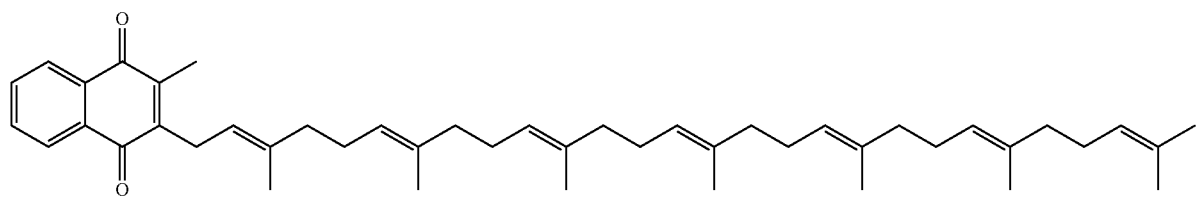

MK-7

SUMMARY

Thus, viewed from one aspect one example of the disclosure provides a compound of formula (I)

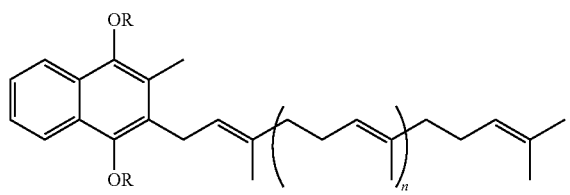

wherein each R is independently hydrogen, a —P(R$^1$)$_y$ group wherein y is 2 or 3, —SO$_2$R$^4$, —COOH, —COOC$_{1-6}$ alkyl, —CON(R$^2$)$_2$, COAr, —COC$_{1-6}$ alkyl group; —CO(CH$_2$)$_p$COOR$^3$, CO(CH$_2$)$_p$CON(R$^2$)$_2$ or —CO(CHR$^6$)$_p$N(R$^5$)$_2$ wherein at least one R group is not hydrogen and wherein both R groups are not COCH$_3$;

each R$^1$ is independently OH, halo, C$_{1-6}$-alkyl, OPh, Obenzyl, OC$_{1-6}$-alkyl or oxo such that the valency of the P atom is 3 or 5;

each R$^2$ group is independently hydrogen or C$_{1-6}$-alkyl;

R$^3$ is H, Ar, or (CH$_2$)$_p$Ar;

R$^4$ is OH, C$_{1-6}$ alkyl, Ph, CF$_3$, or tolyl;

each R$^5$ is H, an amino protecting group such as Boc, or C$_{1-6}$ alkyl;

each R$^6$ is H or C$_{1-6}$ alkyl;

any C$_{1-6}$-alkyl group is optionally substituted by one or more groups selected from —OR$^2$, N(R$^2$)$_2$ or COOR$^2$;

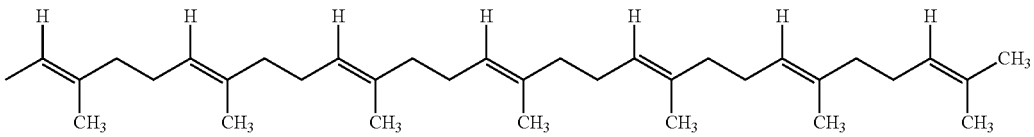 [SMILES: C/C=C(\C)CC/C=C(\C)CC/C=C(\C)CC/C=C(\C)CC/C=C(\C)CC/C=C(\C)CCC=C(C)C]

each Ar is an optionally substituted phenyl or naphthyl group, said substituent being a C$_{1-6}$ alkyl, CHalH$_2$, CHal$_2$H, CHal$_3$, (where Hal is halide), OH, OC$_{1-6}$-alkyl, COOR$^6$;

each p is 1 to 4;

and n is 3 to 8; or a salt or solvate thereof.

Alternatively viewed, an example provides, a compound of formula (I)

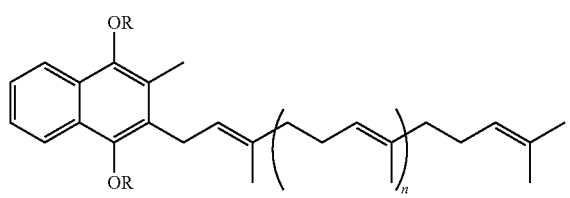

wherein each R is independently hydrogen, a —P(R$^1$)$_y$ group wherein y is 2 or 3, —SO$_2$R$^4$, —COOH, —COOC$_{1-6}$ alkyl, —CON(R$^2$)$_2$, COAr, or —COC$_{1-6}$ alkyl group, preferably —COC$_{2-6}$ alkyl group; wherein at least one R group is not hydrogen;

each R$^1$ is independently OH, halo, C$_{1-6}$-alkyl, OPh, Obenzyl, OC$_{1-6}$-alkyl or oxo such that the valency of the P atom is 3 or 5;

each R$^2$ group is independently hydrogen or C$_{1-6}$-alkyl;

any C$_{1-6}$-alkyl group is optionally substituted by one or more groups selected from —OR$^2$, N(R$^2$)$_2$ or COOR$^2$;

each R$^4$ is OH, C$_{1-6}$ alkyl, Ph, CF$_3$, or tolyl;

each Ar is an optionally substituted phenyl or naphthyl group, said substitutent being a C$_{1-6}$ alkyl;

and n is 3 to 8; or a salt or solvate thereof. It is preferred if both R groups are not COCH$_3$.

Viewed from another aspect an example provides a nutraceutical or pharmaceutical composition comprising a compound of formula (I) or (Ib) as hereinbefore defined, especially for oral administration.

Viewed from another aspect an example provides a compound of formula (I) or (Ib) as hereinbefore defined for use in medicine.

Viewed from another aspect an example provides a compound as hereinbefore defined for use in the treatment of a condition associated with vitamin K2 such as for the treatment of osteoporosis and conditions of the cardiovascular system such as arteriosclerosis.

Viewed from another aspect various examples provide methods of treating a condition associated with vitamin K2 comprising administering to a patient in need thereof an effective amount of a compound of formula (I) as hereinbefore defined.

DETAILED DESCRIPTION

In certain examples, the compounds are preferably analogues of MK-6, MK-7 or MK-8, i.e. n is 4 to 6. MK-9 is also an option, and thus n=7. Most preferably, they are analogues of MK-7 and n is 5. It is thus preferred if the long chain isoprenoid at position 2 on the naphthoquinone ring is The compounds can be mono or disubstituted analogues of formula (I). Thus, both R groups cannot be hydrogen. Where certain example compounds are monosubstituted, the substituent can be present on either ketone position on the naphthoquinone ring (the 1 or 4 positions, where the 1-position is adjacent the isoprenoid chain and 4-position adjacent the methyl group). It is preferred however, in certain examples that the compounds are disubstituted. Whilst one R group may be an acetate, it is preferred if both R groups are not acetate (thus forming —OCOCH$_3$ at the 1 and 4 position).

It is within the scope of this disclosure and certain example compounds for the substituent groups R used in a compounds of formula (I) to be the same or different however, it is preferred if these are different. The use therefore of compounds where the R groups are not the same has been found to offer valuable properties, despite being harder to make synthetically. In particular, these compounds may be more bioavailable in vivo. The use of bis substituted molecules (where R is not H) but where the two R groups are not the same is preferred. Bis substituted compounds are generally more stable.

We have surprisingly found however in the context of mono substituted analogues (where one R is H) that there may be a synergy between the monosubstituted compound and its corresponding MK-n compound. The monosubstituted compound may degrade to its MK-n analogue. It would then be expected that the relatively less stable MK-n compound would degrade rapidly. We do not however observe this. There appears to be a type of synergy between the monosubstituted compounds of formula (I) and the corresponding MK-n analogue whereby the MK-n compound is stabilised against degradation by the presence of the monosubstituted compound.

An example further provides therefore a composition comprising a monosubstituted compound of formula (I) above (i.e. where one R group is H) and an MK-n compound, ideally the composition, e.g. a nutraceutical or pharmaceutical composition, comprises the MK-n compound corresponding to the monosubstituted compound of formula (I). In particular, a composition might comprise MK-7 and a monosubstituted compound of formula (I) where n is 5.

In one embodiment, at least one R is a phosphorus containing —P($R^1$)$_y$ group, i.e. such that the O atom bonds to the phosphorus atom. The phosphorus atom can be in its 3 or 5 valency state, preferably the 5 valency state. Where the P is 5-valent, y is 3 and one $R^1$ group represents oxo thus forming the P=O group. A preferred P group is therefore P(O)($R^7$)$_2$ wherein each $R^7$ is $C_{1-6}$-alkyl, halo, OH, or $OC_{1-6}$alkyl. Ideally, this group is PO(OH)$_2$. In another embodiment, it may be P(=O)O$C_{1-6}$ alkyl)$_2$ such as P=O (OEt$_2$).

Where the P atom is in the 3 valent state, y is 2 and $R^1$ should not be oxo. $R^1$ is preferably OH, $C_{1-6}$-alkyl or O$C_{1-6}$alkyl. Especially preferably, the 3-valent group is —P(O$C_{1-6}$-alkyl)$_2$ or P(OH)$_2$.

In an alternative preferred embodiment, the compounds are mono or diesters. Preferred ester groups are ethyl esters or phenyl esters. The combination of an ester and a phosphorus containing —P($R^1$)$_y$ group is a further preferred option.

A further preferred option is the use of mono or dicarbonates or carbamates, i.e. where in the R group is —COOH or —COO$C_{1-6}$alkyl or where in R group is CON($R^2$)$_2$.

A further preferred embodiment is the use of a sulphate or derivative thereof, i.e. where R is SO$_2R^4$. $R^4$ is preferably OH or represents methyl or tolyl (thus forming mesylate and tosylate).

In any embodiment the group $R^2$ is preferably hydrogen. Any amino group is therefore preferably NH$_2$.

We have also found that the use of R groups of formula —CO(CHR$^6$)$_p$N(R$^5$)$_2$ are preferred. $R^6$ is preferably H or a $C_{1-6}$ alkyl such as C1-4 alkyl group. At least one $R^5$ is preferably H. The other $R^5$ is preferably a protecting group such as Boc (tButyloxycarbonyl). The subscript p is preferably 1 or 2. A preferred group is therefore —CO(CHR$^6$)$_{1/2}$NH($R^5$) where $R^5$ is a protecting group for the amino, e.g. Boc and $R^6$ is H or a $C_{1-6}$ alkyl group.

The use of —CO(CH$_2$)$_p$COOR$^3$ is a further preferred option, especially where $R^3$ is H. The subscript p may preferably be 1-3 in this embodiment.

Ar is preferably Ph or 4-CF$_3$-Ph-.

Where the certain example compounds comprise an alkyl chain, e.g. as part of the ester or as part of an amino group, this alkyl chain may contain a substituent selected from —OR$^2$, N($R^2$)$_2$, or COOR$^2$. This substituent therefore provides polarity to the molecule and aids its dissolution in the body. If present, preferably one such group should be present. Preferably, that group should be OH. Preferably no such substituent is present.

In a further preferred embodiment however, the compounds may comprise at least one ester OCO— at the OR position. That ester is preferably not an acetate. Preferred compounds are of formula (Ia)

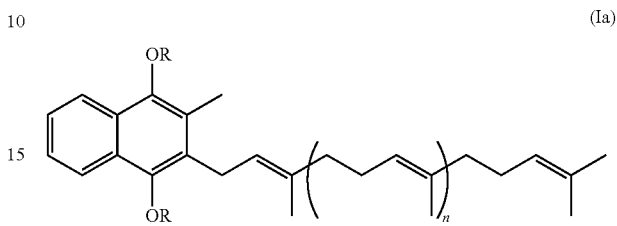

(Ia)

wherein each R is independently hydrogen, a —P($R^1$)$_y$ group wherein y is 2 or 3, COAr, —CO$C_{2-6}$ alkyl group; —CO(CH$_2$)$_p$COOH; or —CO(CHR$^6$)$_p$N(R$^5$)$_2$ wherein at least one R group is not hydrogen and preferably R groups are different;

each $R^1$ is independently OH, halo, $C_{1-6}$-alkyl, OPh, Obenzyl, O$C_{1-6}$-alkyl or oxo such that the valency of the P atom is 3 or 5;

each $R^5$ is H, an amino protecting group such as Boc, or $C_{1-6}$ alkyl;

$R^6$ is H or $C_{1-6}$ alkyl;

any $C_{1-6}$-alkyl group is optionally substituted by one or more groups selected from —OR$^2$, N($R^2$)$_2$ or COOR$^2$;

each Ar is an optionally substituted phenyl or naphthyl group, said substituent being a $C_{1-6}$ alkyl CHalH$_2$, CHal$_2$H, CHal$_3$, OH, O$C_{1-6}$-Alkyl, COOR$^6$;

each p is 1 to 4;

and n is 4 to 7; or a salt or solvate thereof.

Preferred example compounds are of formula (II) to (IV):

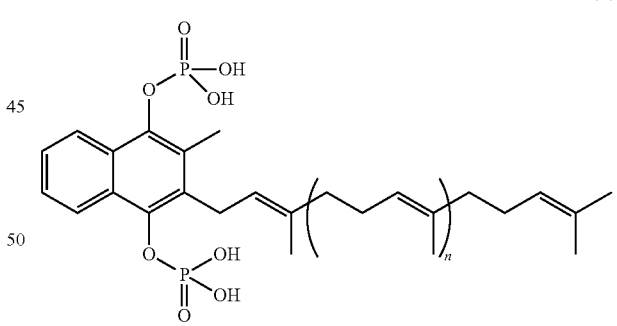

(II)

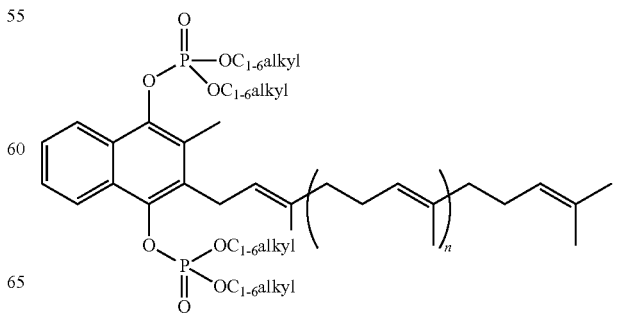

(III)

-continued (IV)

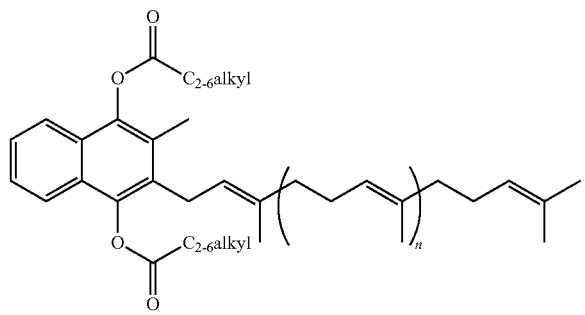

where n is 3 to 8, such as 4 to 7, preferably 4 to 6;
or the monosubstituted analogues of these compounds.
Further preferred compounds are those of formula (V)

(V)

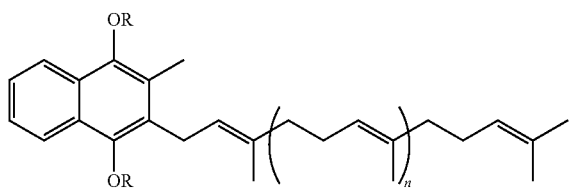

wherein one R is independently hydrogen, a —P($R^1$)$_y$ group wherein y is 2 or 3; —CO($CH_2$)$_p$COOH; or —CO(CHR$^6$)$_p$N($R^5$)$_2$;

and one R is COAr or —CO$C_{1-6}$ alkyl group;

each $R^1$ is independently OH, halo, $C_{1-6}$-alkyl, OPh, Obenzyl, O$C_{1-6}$-alkyl or oxo such that the valency of the P atom is 3 or 5;

each $R^5$ is H, an amino protecting group such as Boc, or $C_{1-6}$ alkyl;

$R^6$ is H or $C_{1-6}$ alkyl;

each Ar is an optionally substituted phenyl or naphthyl group, said substitutent being a $C_{1-6}$ alkyl CHal$H_2$, CHal$_2$H, CHal$_3$, OH, O$C_{1-6}$-Alkyl, COO$R^6$;

each p is 1 to 4;

and n is 4 to 7; or a salt or solvate thereof.

It has surprisingly been found that the certain example compounds have a much longer shelf life than their corresponding diketone vitamin K2 analogue. Without wishing to be limited by theory, it is envisaged that the claimed compounds are less susceptible to oxidation.

It is important however, that the OR group is capable of hydrolysis and oxidation within the body to yield the native MK-n analogue and hence vitamin K2 type structure. The claimed structures are all based on readily hydrolysable ester type linkages.

Synthesis

Certain example compounds can be synthesized from the corresponding menaquinone compound, e.g. MK-7. Menaquinone compounds of use as starting materials can be prepared following the protocols of WO2010/035000 which is herein incorporated by reference. Naturally occurring vitamin K2 could also be used here. It will be appreciated therefore that the starting menaquinone reactant might contain a mixture of different MK-n compounds (where n is the chain length). Naturally occurring vitamin K2 is formed from chains of differing lengths.

The current disclosure therefore covers a composition in which there are a mixture of compounds of formula (I) as hereinbefore defined in which the value of n varies, e.g. a mixture comprising MK-6, MK-7 and MK-8 analogues of formula (I).

The incorporation of an ester group on the ketone functionality of the ring can be achieved by treatment in the presence of, for example, an anhydride and zinc such as Ac$_2$O/Zn. The presence of a base such as sodium acetate also helps the synthesis. Other anhydrides of use include, inter alia, propionic anhydride and so on. The general protocol is summarised in scheme 1

Scheme 1

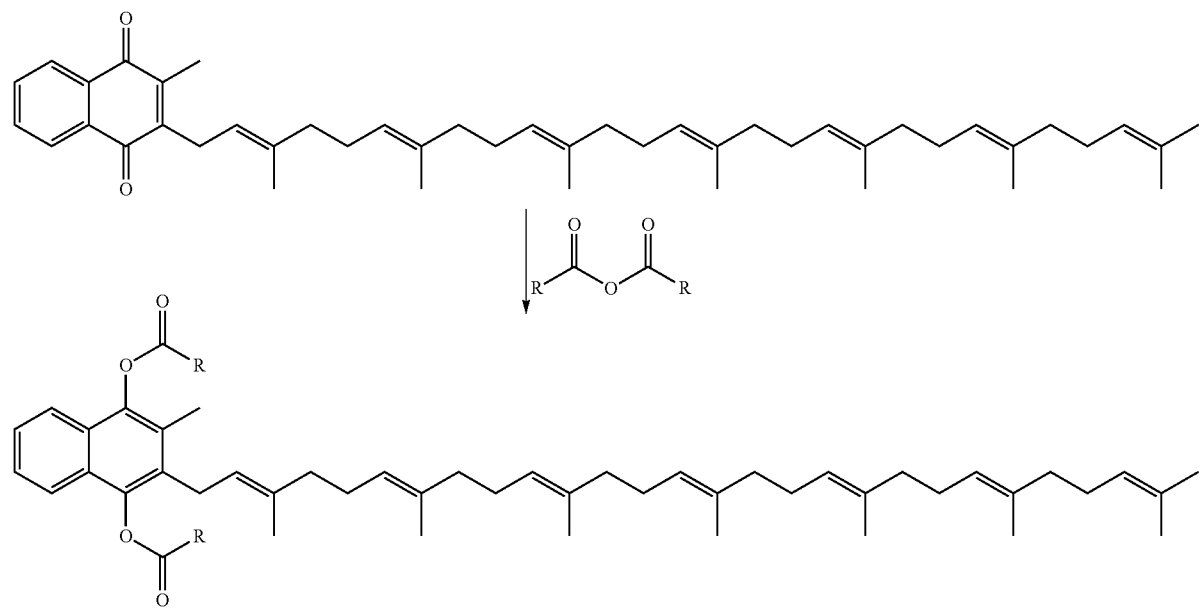

The synthesis of phosphorus compounds can be achieved by following the protocols in scheme 2:

Scheme 2

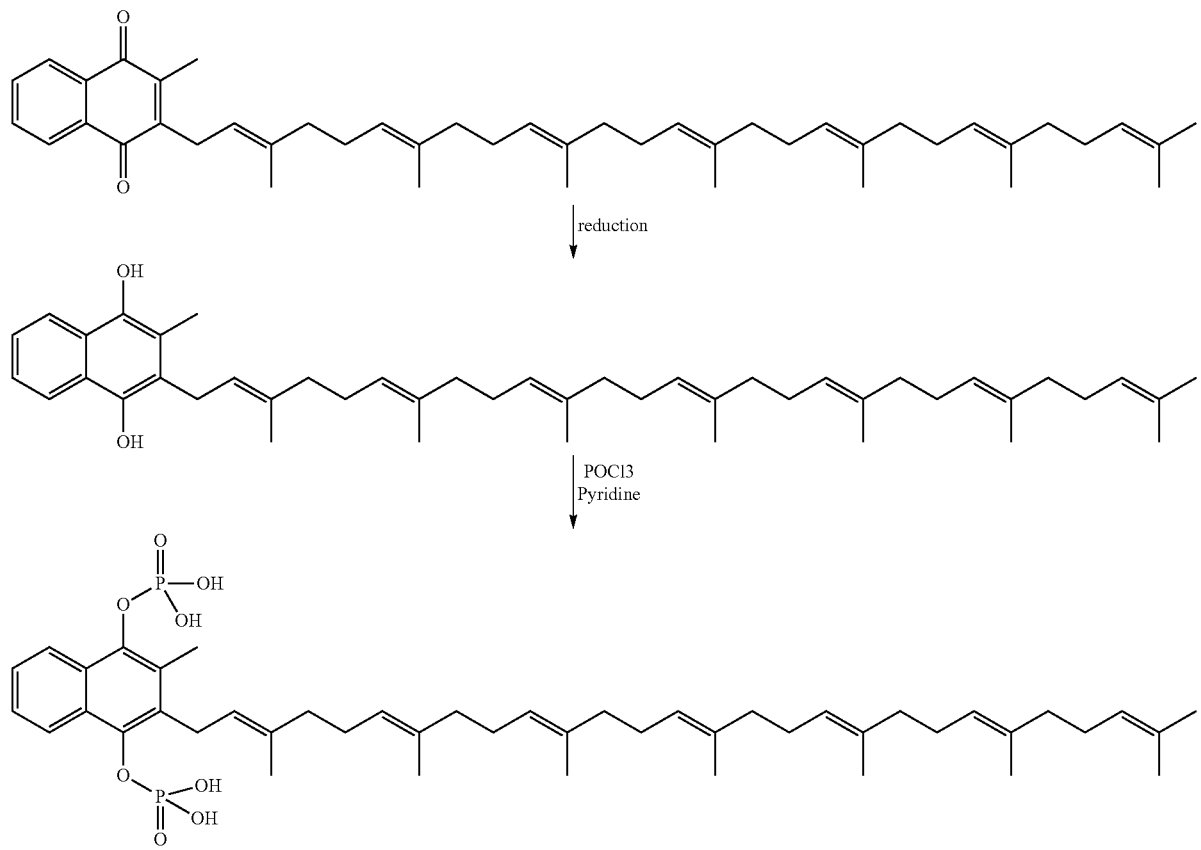

Thus, the naphthoquinone ring can be reduced using a convenient reducing agent (that does not affect the stereochemistry in the isoprenoid chain) and then reacted with, for example $POCl_3$. Reduction of the naphthoquinone also allows the formation of the sulphates, carbonates and carbamates mentioned above using simple chemistry. Once a relatively nucleophilic hydroxyl group has been created on the ring, then all manner of known chemistry becomes available to the skilled person using well known nucleophilic substitution reactions with standard electrophiles.

The formation of monosubstituted compounds is conveniently achieved by selective hydrolysis of the disubstituted compound. It has been found that the OR group adjacent to the isoprenoid chain hydrolyses faster than the OR group adjacent to the methyl group. That allows selective hydrolysis to occur and allows therefore the formation of a mono-substituted type structure.

If the desired monosubstitution contains the ester group at the 4-position on the ring (adjacent the isoprenoid chain), that can be achieved by careful control during the esterification (or other addition) type process. The 4-position ketone group will esterify slightly faster than that at the 1-position group. Using stoichiometric amounts of reactant can therefore encourage monosubstitution at the 4-position.

It will be appreciated that the OR groups might be added before the final molecule synthesis is completed. In particular, the present inventors have previously taught a process for the manufacture of vitamin K2 relying on Kumada or Suzuki chemistry to couple isoprenoid chains to naphthoquinone rings. That chemistry could be employed here.

It is preferred in WO2010/035000, if the 7 unit isoprenoid chain of MK-7 is developed by coupling a pentraprenol to a naphthoquinone carrying 2-isoprenoid units. The key intermediate in this process can be provided with the OR groups before being coupled to the pentaprenol. The key intermediate in the synthesis is therefore of formula (VII):

(VII)

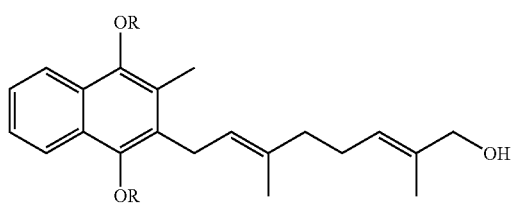

wherein R is as hereinbefore defined. In order to couple this compound to a pentaprenol type structure, it is useful to convert the hydroxyl group to a better leaving group, especially a halo group. A further aspect of the current example therefore relates to the compound of formula (VI):

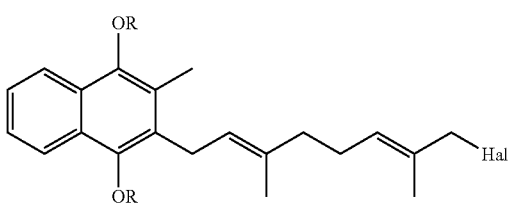

(VI)

wherein Hal is a halide, especially bromide and R is as hereinbefore defined.

The skilled person will be able to devise various procedures for introducing the necessary R groups onto the compounds of formula (I). For example, the skilled person could follow the ideas in scheme 3:

The compounds of formula (I) may also be present as salts. Salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are included within the ambit of certain examples.

The pharmaceutically acceptable salts are defined to comprise the therapeutically active non-toxic acid addition salt forms that the compounds according to formula (I) are able to form. Said salts can be obtained by treating the base form of the compounds according to formula (I) with appropriate acids, for example inorganic acids, for example hydrohalic acid, in particular hydrochloric acid, hydrobromic acid, sulphuric acid, nitric acid and phosphoric acid; organic acids, for example acetic acid, hydroxyacetic acid, pro-

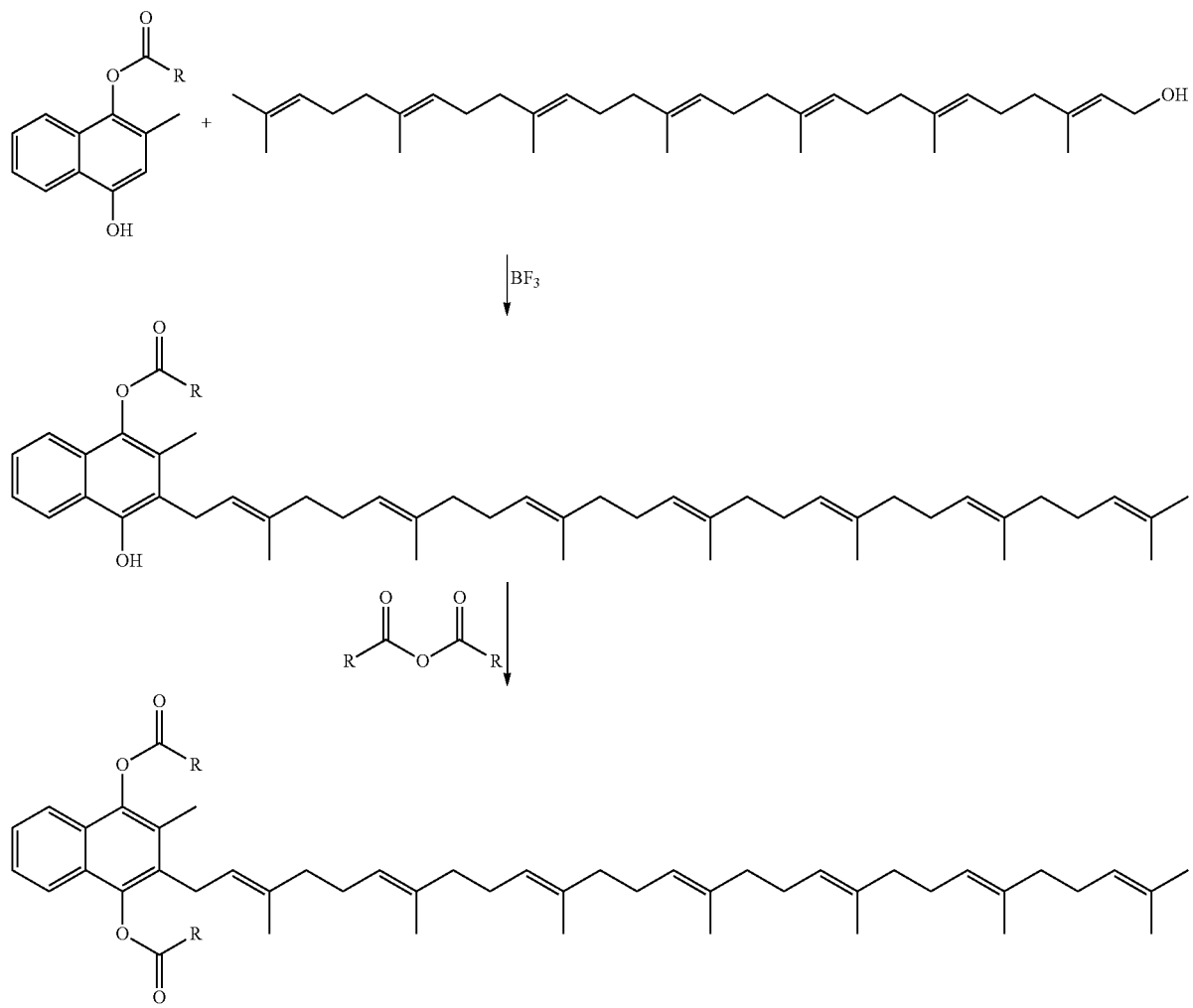

Scheme 3

In this scheme, a monosubstituted naphthoquinone is coupled with the seven member isoprenoid chain and then a further carboxyl group is coupled to the free hydroxyl. It will be appreciated therefore that there are many options available to the skilled person here.

panoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicylic acid, p-aminosalicylic acid and pamoic acid.

Conversely said acid salt forms can be converted into the free base form by treatment with an appropriate base.

The compounds according to formula (I) containing acidic protons may also be converted into their therapeutically active non-toxic base salt forms by treatment with appropriate organic and inorganic bases. Appropriate base salt forms comprise, for example, the ammonium salts, the alkaline and earth alkaline metal salts, in particular lithium, sodium, potassium, magnesium and calcium salts, salts with organic bases, e.g. the benzathine, N-methyl-D-glucamine, hybramine salts, and salts with amino acids, for example arginine and lysine.

Conversely, said base salt forms can be converted into the free acid forms by treatment with an appropriate acid.

The pharmaceutically acceptable acid addition salt forms of the compounds of formula (I) are the preferred pharmaceutically acceptable salt forms of the compounds of formula (I).

Various examples also encompass solvates of the compounds of formula (I). The term solvate comprises the solvent addition forms of the base compound as well as the pharmaceutically acceptable salts thereof, which the compounds of formula (I) are able to form. Examples of such solvent addition forms are e.g. hydrates, alcoholates and the like.

Applications

Vitamin K2 and hence MK-7 has well documented therapeutic applications and the prodrugs of vitamin K2 produced in certain examples are suitable for all known therapeutic applications of vitamin K2. It can also be used as a food supplement or in any nutraceutical product, e.g. as a vitamin supplement.

Conditions in which vitamin K2 administration may assist treatment include osteoporosis and bone related disorders, cardiovascular health in general such as arteriosclerosis, myocardial infarction, calcification of blood vessels, diabetes, male infertility, conditions associated with inflammation and so on.

Example compounds may be utilized alone or in combination with one or more other drugs in the treatment, prevention, control, amelioration, or reduction of risk of diseases or conditions for which compounds of Formula (I) may have utility.

The formed compounds may therefore be formulated as pharmaceutically acceptable compositions or nutraceutically acceptable compositions using known excipients. Certain example compounds may also be used in combination therapy with other active agents.

While it is possible that certain example compounds may be administered as the bulk substance, it is preferable to present the active ingredient in a pharmaceutical formulation, for example, wherein the agent is in admixture with a pharmaceutically acceptable carrier/excipient selected with regard to the intended route of administration and standard pharmaceutical practice.

The term "carrier" or "excipient" refers to a diluent, and/or vehicle with which an active compound is administered. Certain example compositions may contain combinations of more than one carrier. Such carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition. The choice of pharmaceutical carrier can be selected with regard to the intended route of administration and standard pharmaceutical practice. The pharmaceutical compositions may comprise as, in addition to, the carrier any suitable binder(s), lubricant(s), suspending agent(s), coating agent(s), and/or solubilizing agent(s).

It will be appreciated that pharmaceutical compositions for use in accordance with the present examples may be in the form of oral, parenteral, transdermal, inhalation, sublingual, topical, implant, nasal, or enterally administered (or other mucosally administered) suspensions, capsules or tablets, which may be formulated in conventional manner using one or more pharmaceutically acceptable carriers or excipients. Oral administration is preferred, especially in tablet form or capsule form.

It is a major advantage that the prodrugs as claimed herein are more polar than MK-7 itself. That makes the compounds more easy to formulate and may increase their bioavailability within the body. Some compounds may even be water soluble although others may at least dissolve in a water/alcohol mixture. We have shown that our compound provide a long lasting effect within the body. In our rat model, we have shown that after 12 hrs, certain example compounds are able to provide the same level of active component as MK-7 itself. This makes the compounds attractive for example for once a day administration.

There may be different composition/formulation requirements depending on the different delivery systems. Likewise, if the composition comprises more than one active component, then those components may be administered by the same or different routes.

The pharmaceutical formulations of the present examples can be liquids that are suitable for oral, mucosal and/or parenteral administration, for example, drops, syrups, solutions, injectable solutions that are ready for use or are prepared by the dilution of a freeze-dried product but are preferably solid or semisolid as tablets, capsules, granules, powders, pellets, pessaries, suppositories, creams, salves, gels, ointments; or solutions, suspensions, emulsions, or other forms suitable for administration by the transdermal route or by inhalation.

Certain example compounds can be administered for immediate-, delayed-, modified-, sustained-, pulsed- or controlled-release applications.

In one aspect, oral compositions are slow, delayed or positioned release (e.g., enteric especially colonic release) tablets or capsules.

Oral administration is preferred. Examples of pharmaceutically acceptable disintegrants for oral compositions useful in the present examples include, but are not limited to, starch, pre-gelatinized starch, sodium starch glycolate, sodium carboxymethylcellulose, croscarmellose sodium, microcrystalline cellulose, alginates, resins, surfactants, effervescent compositions, aqueous aluminium silicates and crosslinked polyvinylpyrrolidone.

Examples of pharmaceutically acceptable binders for oral compositions useful herein include, but are not limited to, acacia; cellulose derivatives, such as methylcellulose, carboxymethylcellulose, hydroxypropylmethylcellulose, hydroxypropylcellulose or hydroxyethylcellulose; gelatin, glucose, dextrose, xylitol, polymethacrylates, polyvinylpyrrolidone, sorbitol, starch, pre-gelatinized starch, tragacanth, xanthane resin, alginates, magnesium-aluminum silicate, polyethylene glycol or bentonite.

Examples of pharmaceutically acceptable fillers for oral compositions include, but are not limited to, lactose, anhydrolactose, lactose monohydrate, sucrose, dextrose, mannitol, sorbitol, starch, cellulose (particularly microcrystalline cellulose), dihydro- or anhydro-calcium phosphate, calcium carbonate and calcium sulfate.

Examples of pharmaceutically acceptable lubricants useful in certain example compositions include, but are not limited to, magnesium stearate, talc, polyethylene glycol, polymers of ethylene oxide, sodium lauryl sulfate, magnesium lauryl sulfate, sodium oleate, sodium stearyl fumarate, and colloidal silicon dioxide.

Examples of suitable pharmaceutically acceptable odorants for the oral compositions include, but are not limited to, synthetic aromas and natural aromatic oils such as extracts of oils, flowers, fruits (e.g., banana, apple, sour cherry, peach) and combinations thereof, and similar aromas. Their use depends on many factors, the most important being the organoleptic acceptability for the population that will be taking the pharmaceutical compositions.

Examples of suitable pharmaceutically acceptable dyes for the oral compositions include, but are not limited to, synthetic and natural dyes such as titanium dioxide, beta-carotene and extracts of grapefruit peel.

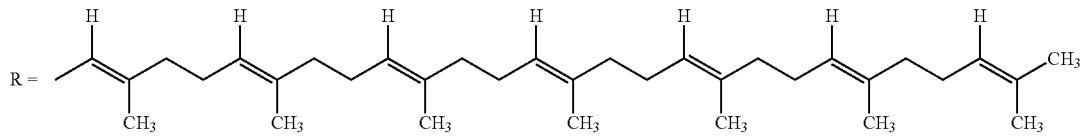 [SMILES: C/C=C(\C)CC/C=C(\C)CC/C=C(\C)CC/C=C(\C)CC/C=C(\C)CC/C=C(\C)CCC=C(C)C]

Suitable examples of pharmaceutically acceptable sweeteners for the oral compositions include, but are not limited to, aspartame, saccharin, saccharin sodium, sodium cyclamate, xylitol, mannitol, sorbitol, lactose and sucrose. Suitable examples of pharmaceutically acceptable buffers include, but are not limited to, citric acid, sodium citrate, sodium bicarbonate, dibasic sodium phosphate, magnesium oxide, calcium carbonate and magnesium hydroxide.

Suitable examples of pharmaceutically acceptable surfactants include, but are not limited to, sodium lauryl sulfate and polysorbates.

Suitable examples of pharmaceutically acceptable preservatives include, but are not limited to, various antibacterial and antifungal agents such as solvents, for example ethanol, propylene glycol, benzyl alcohol, chlorobutanol, quaternary ammonium salts, and parabens (such as methyl paraben, ethyl paraben, propyl paraben, etc.).

Suitable examples of pharmaceutically acceptable stabilizers and antioxidants include, but are not limited to, ethylenediaminetetriacetic acid (EDTA), thiourea, tocopherol and butyl hydroxyanisole.

The compounds of formula (I) have utility in, inter alia, the treatment of osteoporosis, cancer, diabetes, male infertility or cardio-vascular disease. The compounds may also be used as vitamin supplements or in any other known application of vitamin K2, e.g. for injection into new-born infants to aid blood clotting.

Certain example compounds may be taken once a day, twice a day, more often or less often depending on the purpose of administration, preferably once a day. It is particularly preferred that analogues of MK-7 can be administered once a day whereas analogues of other menaquinones such as Mk-4 cannot.

The dose and the administration frequency will also depend on the use in question, e.g. whether for clinical use or via a supplement. A dosage of 20 to 250 micro g/day is suitable as a food supplement. A dosage of 120-1200 micro g/day may suitable as a pharmaceutical product.

In particular, certain example compounds can be used in food fortification, e.g. of natto.

A further major advantage of the presence compounds is that they may be taken at any time. Conventional vitamin K2 supplements are taken with meals as consuming them along with fat enhances the bioavailability of the vitamin K2 in the body. Many consumers, however, fail to remember to take the product with a meal or perhaps eat the vitamin K2 supplement with a meal such as breakfast which often has almost no fat in it. The bioabsorption of the vitamin K2 supplement is therefore reduced in these circumstances.

Certain example compounds are less dependent on the presence of fat and offer the ability to be taken at any time or with breakfast as there is no requirement to administer the compounds with a fatty additive.

The aspects of the present disclosure will now be further described with reference to the following non limiting examples.

In the examples which follow:

Example 1

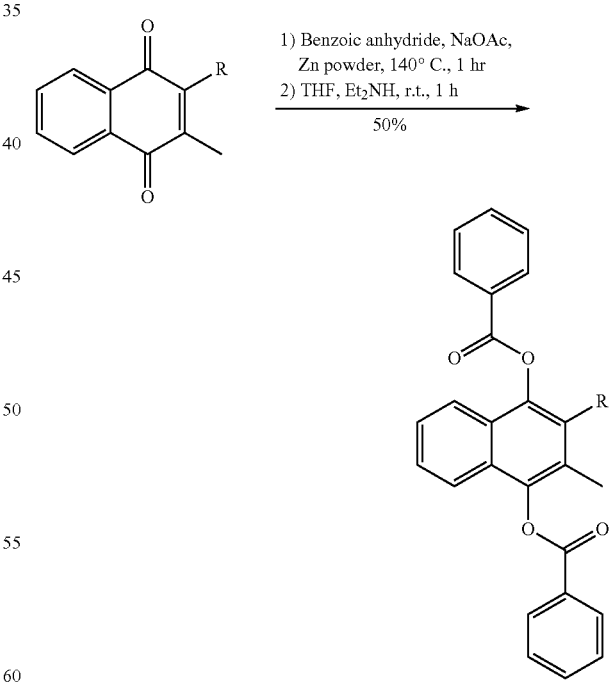

2-((2E,6E,10E,14E,18E,22E)-3,7,11,15,19,23,27-Heptamethyloctacosa-2,6,10,14,18,22,26-heptaen-1-yl)-3-methylnaphthalene-1,4-dione (1.00 g, 1.34 mmol), benzoic anhydride (6.00 g, 26.52 mmol), NaOAc (0.134 g, 1.64 mmol) and Zn powder (0.31 g, 4.74 mmol) were added together and heated to 140° C. After 1 h at 140° C. the reaction mixture was cooled down to r.t. and diluted with THF (40 mL). Et$_2$NH (20 mL) was added and the reaction mixture was stirred for another hour after which heptane (50 mL) was added. The resulting mixture was filtrated and the solvent was removed under reduced pressure. The crude product was purified by flash chromatography (heptane:EtOAc gradient) to obtain 0.58 (50%) of 2-((2E,6E,10E,14E,18E,22E)-3,7,11,15,19,23,27-heptamethyl-octacosa-2,6,10,14,18,22,26-heptaen-1-yl)-3-methylnaphthalene-1,4-diyl dibenzoate as a dark yellow oil.

$^1$H NMR (400 MHz, CDCl$_3$) δ 8.34 (t, J=7.8, 4H), 7.80-7.65 (m, 4H), 7.62-7.52 (m, 4H), 7.44-7.36 (m, 2H), 5.18-5.00 (m, 7H), 3.60-3.38 (m, 2H), 2.31 (s, 3H), 2.12-1.85 (m, 23H), 1.66 (s, 3H), 1.63-1.47 (m, 22H).

$^{13}$C NMR (101 MHz, CDCl$_3$) δ 166.51, 143.06, 142.86, 136.49, 135.36, 135.15, 135.12, 134.04, 134.02, 133.95, 131.46, 130.90, 130.64, 129.42, 129.39, 129.02, 128.95, 127.49, 126.76, 126.63, 126.53, 124.64, 124.64, 124.46, 124.25, 121.78, 121.57, 121.40, 39.97, 39.95, 39.84, 27.38, 27.38, 27.00, 26.96, 26.94, 26.91, 26.79, 25.91, 25.91, 17.90, 16.57, 16.57, 16.26, 16.24, 16.22, 13.45.

MS: m/z [M+Na]$^+$ calcd for C$_{60}$H$_{74}$NO$_4$: 881.5485; found: 881.4.

Example 2

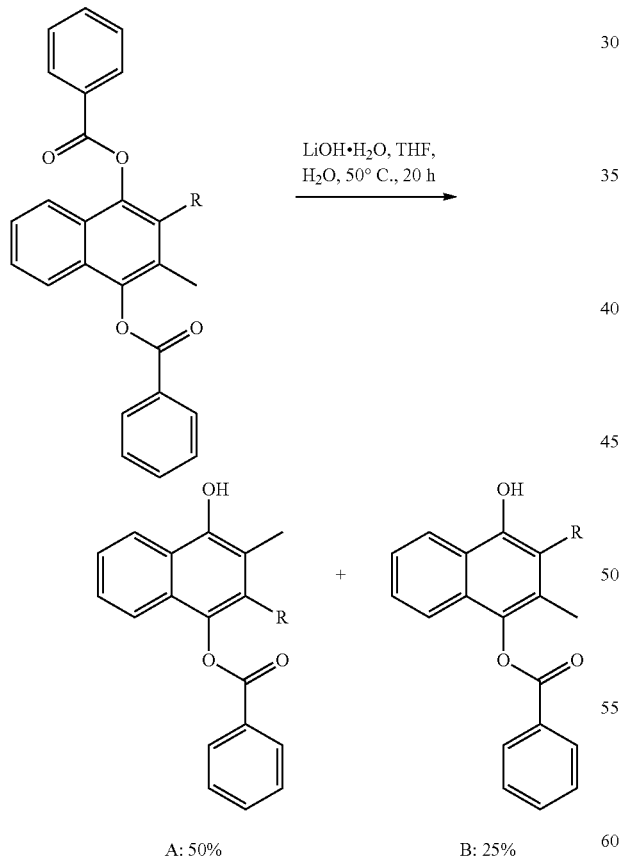

A: 50%  B: 25%

To a solution of 2-((2E,6E,10E,14E,18E,22E)-3,7,11,15,19,23,27-heptamethyloctacosa-2,6,10,14,18,22,26-heptaen-1-yl)-3-methylnaphthalene-1,4-diyl dibenzoate (4.71 g, 5.48 mmol) in a mixture of THF (75 mL) and H$_2$O (20 mL) LiOH.H$_2$O (1.84 g, 443.8 mmol) was added. The resulting solution was degassed in an ultrasonic bath for 5 min and stirred at 50° C. for 20 h after which 3 M HCl (aq) was added until pH 2. The resulting mixture was extracted with EtOAc (2×250 mL). The organic layers were combined, dried (Na$_2$SO$_4$), filtrated and the solvent was removed under reduced pressure. The crude product was purified by flash chromatography (heptane:EtOAc gradient) to obtain 2.30 g (50%) of 2-((2E,6E,10E,14E,18E,22E)-3,7,11,15,19,23,27-heptamethyloctacosa-2,6,10,14,18,22,26-heptaen-1-yl)-4-hydroxy-3-methylnaphthalen-1-yl benzoate (A) and 1.18 g (25%) of 3-((2E,6E,10E,14E,18E,22E)-3,7,11,15,19,23,27-heptamethyloctacosa-2,6,10,14,18,22,26-heptaen-1-yl)-4-hydroxy-2-methylnaphthalen-1-yl benzoate (B).

MS: m/z [M+Na]$^+$ calcd for C$_{53}$H$_{70}$NO$_3$: 777.5223; found: 777.5.

NMR data of product A $^1$H NMR (400 MHz, CDCl$_3$) δ 8.39 (d, J=8.0, 2H), 8.21-8.12 (m, 1H), 7.75-7.56 (m, 2H), 7.51 (t, J=7.7, 2H), 7.43-7.38 (m, 2H), 5.21-5.05 (m, 7H), 3.44 (s, 2H), 2.21 (s, 3H), 2.17-1.93 (m, 25H), 1.71 (s, 3H), 1.69-1.54 (m, 21H).

$^{13}$C NMR (101 MHz, CDCl$_3$) δ 166.15, 147.19, 138.20, 135.31, 135.17, 135.14, 135.10, 134.00, 133.96, 131.44, 130.65, 130.43, 129.56, 128.91, 128.69, 126.28, 126.13, 125.24, 124.64, 124.50, 124.43, 124.24, 124.14, 121.82, 121.63, 121.18, 117.55, 39.94, 39.85, 27.37, 26.97, 26.93, 26.90, 26.77, 25.90, 17.89, 16.55, 16.23, 16.21, 12.14.

NMR date of product B $^1$H NMR (400 MHz, CDCl$_3$) δ 8.36 (d, J=7.6, 2H), 8.15-8.10 (m, 1H), 7.69 (t, J=7.3, 2H), 7.57 (t, J=7.6, 2H), 7.43-7.36 (m, 2H), 5.18-5.03 (m, 7H), 3.48 (s, 2H), 2.29 (s, 3H), 2.16-1.90 (m, 25H), 1.85 (s, 3H), 1.68 (s, 3H), 1.61-1.51 (m, 18H).

$^{13}$C NMR (101 MHz, CDCl$_3$) δ 165.34, 147.92, 139.02, 138.07, 135.78, 134.99, 134.93, 134.92, 134.89, 133.72, 131.24, 130.39, 129.37, 128.75, 126.35, 126.27, 124.93, 124.45, 124.31, 124.23, 124.15, 123.52, 121.82, 121.26, 120.69, 120.05, 39.77, 39.75, 39.72, 39.68, 26.80, 26.76, 26.73, 26.70, 26.67, 26.38, 25.71, 17.70, 16.40, 16.13, 16.04, 16.03, 13.61.

Example 3

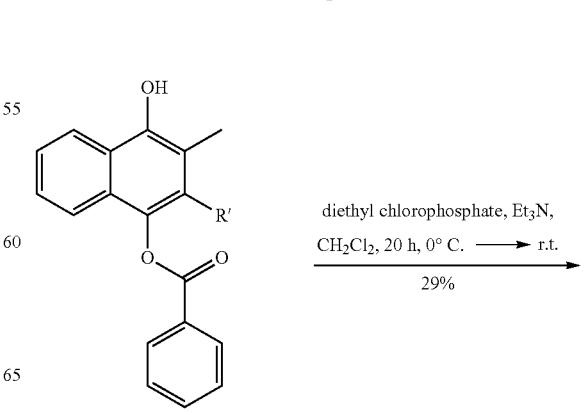

19

-continued

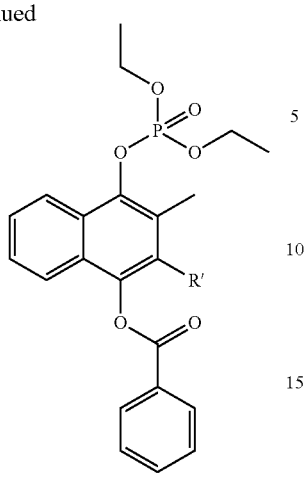

2-((2E,6E,10E,14E,18E,22E)-3,7,11,15,19,23,27-Heptamethyloctacosa-2,6,10,14,18,22,26-heptaen-1-yl)-4-hydroxy-3-methylnaphthalen-1-yl benzoate (0.21 g, 0.28 mmol) was dissolved in $CH_2Cl_2$ (10 mL) and cooled to 0° C. To this solution diethyl chlorophosphate (60 μL, 0.42 mmol) and $Et_3N$ (59 μL, 0.42 mmol) were added. The reaction mixture was stirred at r.t. for 20 h after which the solvent was removed under reduced pressure. The crude product was purified by flash chromatography (heptane:EtOAc gradient) to obtain 70 mg (29%) of 4-((diethoxyphosphoryl)oxy)-2-((2E,6E,10E,14E,18E,22E)-3,7,11,15,19,23,27-heptamethyloctacosa-2,6,10,14,18,22,26-heptaen-1-yl)-3-methylnaphthalen-1-yl benzoate as a colourless oil.

$^1$H NMR (400 MHz, $CDCl_3$) δ 8.31 (d, J=8.0, 2H), 8.21 (d, J=8.5, 1H), 7.70-7.64 (m, 2H), 7.55 (t, J=7.7, 2H), 7.48 (t, J=7.6, 1H), 7.44-7.35 (m, 1H), 5.17-4.99 (m, 7H), 4.28-4.07 (m, 4H), 3.45 (d, J=25.3, 2H), 2.49 (s, 3H), 2.12-1.86 (m, 24H), 1.66 (s, 3H), 1.63-1.52 (m, 21H), 1.28 (t, J=7.1, 6 H).

$^{13}$C NMR (101 MHz, $CDCl_3$) δ 165.26, 142.90, 142.81, 142.14, 142.12, 136.49, 135.32, 135.13, 135.11, 135.10, 135.07, 133.97, 131.41, 131.06, 131.03, 130.58, 129.37, 128.92, 126.98, 126.98, 126.93, 126.87, 126.84, 126.56, 126.53, 126.22, 124.62, 124.48, 124.41, 124.21, 122.94, 121.31, 121.28, 64.97, 64.91, 39.94, 39.93, 39.84, 27.39, 26.98, 26.93, 26.91, 26.90, 26.88, 26.82, 25.89, 17.87, 16.56, 16.36, 16.29, 16.21, 16.21, 16.19, 14.07.

MS: m/z [M+Na]$^+$ calcd for $C_{57}H_{79}O_6P$: 913.5512; found: 913.5.

Example 4

20

-continued

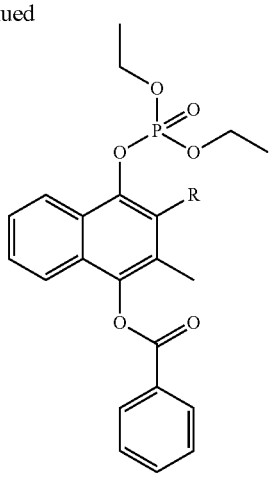

3-((2E,6E,10E,14E,18E,22E)-3,7,11,15,19,23,27-Heptamethyloctacosa-2,6,10,14,18,22,26-heptaen-1-yl)-4-hydroxy-2-methylnaphthalen-1-yl benzoate (0.2 g, 0.26 mmol) was dissolved in $CH_2Cl_2$ (10 mL) and cooled to 0° C. To this solution diethyl chlorophosphate (57 μL, 0.40 mmol) and $Et_3N$ (56 μL, 0.40 mmol) were added. The reaction mixture was stirred at r.t. for 20 h after which the solvent was removed under reduced pressure. The crude product was purified by flash chromatography (heptane:EtOAc gradient) to obtain 0.184 g (79%) of 4-((ethoxy(((2E,6E,10E,14E,18E,22E)-3,7,11,15,19,23,27-heptamethyl-octacosa-2,6,10,14,18,22,26-heptaen-1-yl)oxy)phosphoryl)oxy)-3-ethyl-2-methylnaphthalen-1-yl benzoate as a colourless oil.

$^1$H NMR (300 MHz, $CDCl_3$) δ 8.35-8.29 (m, 2H), 8.28-8.18 (m, 1H), 7.77-7.63 (m, 2H), 7.64-7.51 (m, 2H), 7.52-7.36 (m, 2H), 5.24-4.93 (m, 7H), 4.37-4.06 (m, 4H), 3.82-3.64 (m, 2H), 2.26 (s, 3H), 2.13-1.86 (m, 24H), 1.78 (s, 3H), 1.66 (s, 3H), 1.61-1.52 (m, 18H), 1.34 (t, J=7.1, 6 H).

$^{13}$C NMR (101 MHz, $CDCl_3$) δ 164.82, 142.51, 142.42, 142.34, 142.32, 136.19, 135.30, 135.08, 135.06, 135.04, 133.99, 131.38, 130.53, 130.41, 130.36, 129.30, 128.96, 127.76, 127.74, 126.73, 126.71, 126.68, 126.68, 126.67, 126.61, 126.07, 124.60, 124.47, 124.41, 124.21, 123.19, 122.00, 121.03, 64.97, 64.91, 39.91, 27.26, 26.96, 26.91, 26.89, 26.86, 25.87, 17.86, 16.61, 16.34, 16.27, 16.19, 13.45.

MS: m/z [M+Na]$^+$ calcd for $C_{57}H_{79}O_6P$: 913.5512; found: 913.5.

Example 5

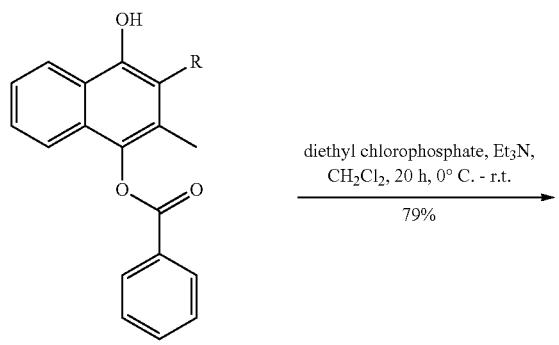

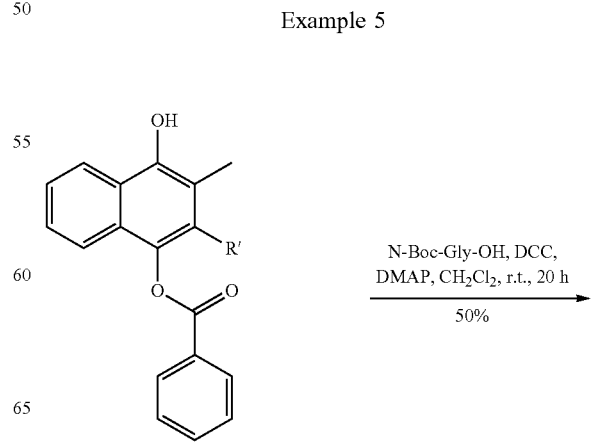

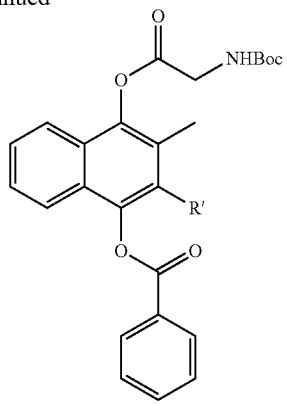

N-Boc-Gly-OH (86 mg, 0.40 mmol), DMAP (57 mg, 0.47 mmol) and DCC (97 mg, 0.47 mmol) were added to a solution of 2-((2E,6E,10E,14E,18E,22E)-3,7,11,15,19,23,27-heptamethyloctacosa-2,6,10,14,18,22,26-heptaen-1-yl)-4-hydroxy-3-methylnaphthalen-1-yl benzoate (0.20 g, 0.26 mmol) in CH₂Cl₂ (6 mL). The reaction mixture was stirred at r.t. for 20 h after which the mixture was diluted with Et₂O (20 mL). The organic solution was then washed with 5% citric acid (15 mL) and brine (10 mL), dried (Na₂SO₄), filtered and the solvent was removed under reduced pressure. The crude product was purified by flash chromatography (heptane:EtOAc gradient) to obtain 0.12 g (50%) of 4-(((tert-butoxycarbonyl)glycyl)oxy)-2-((2E,6E,10E,14E,18E,22E)-3,7,11,15,19,23,27-heptamethyloctacosa-2,6,10,14,18,22,26-heptaen-1-yl)-3-methylnaphthalen-1-yl benzoate as a light yellow solid.

$^1$H NMR (400 MHz, CDCl$_3$) δ 8.31 (d, J=7.8, 2H), 8.11 (d, J=7.8, 2H), 7.75-7.64 (m, 2H), 7.50-7.37 (m, 3H), 5.18 (s, 1H), 5.15-5.00 (m, 7H), 4.43-4.30 (m, 2H), 3.54-3.34 (m, 2H), 2.27 (s, 3H), 2.13-1.87 (m, 24H), 1.70 (s, 3H), 1.61-1.53 (m, 21H), 1.48 (s, 9H).

$^{13}$C NMR (101 MHz, CDCl$_3$) δ 171.39, 165.03, 155.86, 142.81, 142.25, 136.40, 135.15, 133.82, 133.71, 131.24, 130.64, 130.41, 130.20, 129.36, 129.11, 128.74, 128.48, 127.02, 126.17, 124.43, 124.00, 121.55, 120.98, 80.39, 42.46, 39.75, 39.73, 39.71, 39.62, 28.34, 27.11, 26.79, 26.74, 26.72, 26.70, 26.69, 26.60, 25.70, 17.69, 16.37, 16.01, 13.19.

MS: m/z [M+Na]$^+$ calcd for C$_{60}$H$_{81}$NO$_6$: 934.5962; found: 934.6.

Example 6

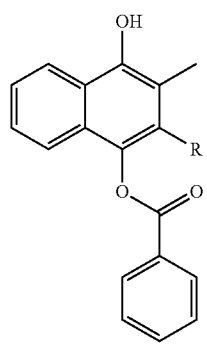

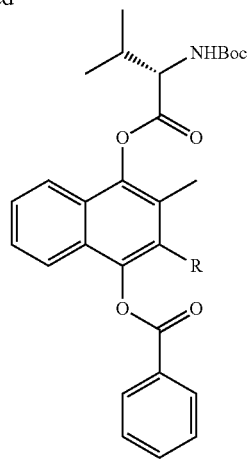

N-Boc-Val-OH (78 mg, 0.36 mmol), DMAP (53 mg, 0.43 mmol) and DCC (89 mg, 0.43 mmol) were added to a solution of 2-((2E,6E,10E,14E,18E,22E)-3,7,11,15,19,23,27-heptamethyloctacosa-2,6,10,14,18,22,26-heptaen-1-yl)-4-hydroxy-3-methylnaphthalen-1-yl benzoate (0.18 g, 0.24 mmol) in CH₂Cl₂ (10 mL). The reaction mixture was stirred at r.t. for 20 h after which the mixture was diluted with Et₂O (20 mL). The organic solution was then washed with 5% citric acid (15 mL) and brine (10 mL), dried (Na₂SO₄), filtered and the solvent was removed under reduced pressure. The crude product was purified by flash chromatography (heptane:EtOAc gradient) to obtain 73 mg (32%) of 4-(((tert-butoxycarbonyl)-L-valyl)oxy)-2-((2E,6E,10E,14E,18E,22E)-3,7,11,15,19,23,27-heptamethyloctacosa-2,6,10,14,18,22,26-heptaen-1-yl)-3-methylnaphthalen-1-yl benzoate as a light yellow solid.

$^1$H NMR (400 MHz, CDCl$_3$) δ 8.31 (d, J=7.7, 2H), 8.10 (d, J=7.7, 2H), 7.72-7.63 (m, 1H), 7.62-7.54 (m, 1H), 7.49-7.35 (m, 3H), 5.20-5.01 (m, 8H), 4.76-4.65 (m, 1H), 3.57-3.34 (m, 2H), 2.63-2.50 (m, 1H), 2.27 (s, 3H), 2.11-1.87 (m, 24H), 1.66 (s, 3H), 1.64-1.52 (m, 21H), 1.48 (s, 9H) 1.17-1.08 (m, 6H).

$^{13}$C NMR (101 MHz, CDCl$_3$) δ 174.26, 170.01, 158.89, 142.77, 141.70, 141.70, 135.85, 135.30, 133.89, 133.89, 133.85, 132.78, 132.42, 130.20, 129.55, 129.38, 129.10, 128.01, 127.70, 127.40, 127.38, 127.30, 125.34, 125.30, 125.22, 123.40, 123.26, 123.21, 122.99, 79.11, 72.57, 57.94, 38.72, 38.70, 38.59, 29.92, 27.33, 26.86, 25.75, 25.71, 25.69, 25.66, 25.58, 24.67, 18.82, 16.65, 15.33, 14.99, 12.29.

MS: m/z [M+Na]$^+$ calcd for C$_{63}$H$_{87}$NO$_6$: 976.6431; found: 976.5.

Example 7

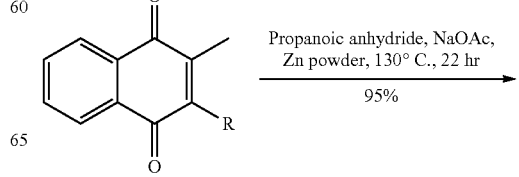

-continued

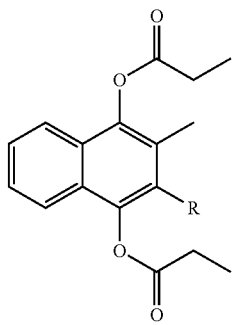

-continued

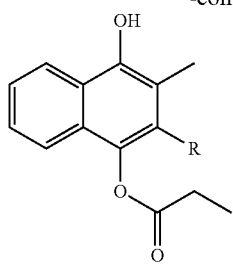 + 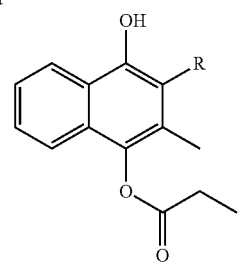

A: 45%  B: 30%

2-((2E,6E,10E,14E,18E,22E)-3,7,11,15,19,23,27-heptamethyloctacosa-2,6,10,14,18,22,26-heptaen-1-yl)-3-methylnaphthalene-1,4-dione (324 mg, 0.50 mmol), propanoic anhydride (7.50 mL, 80 mmol), NaOAc (50 mg, 0.60 mmol) and Zn powder (100 mg, 1.55 mmol) were added together and heated to 130° C. The reaction mixture was stirred for 30 minutes. After cooling to room temperature, the reaction mixture was poured into water and extracted with CHCl$_3$ (×2) and the combined organic phases were dried (Na$_2$SO$_4$), filtrated and the solvent was removed under reduced pressure. The crude product was purified by flash chromatography (heptane:EtOAc gradient) to give 250 mg (66%) of 2-((2E,6E,10E,14E,18E,22E)-3,7,11,15,19,23,27-heptamethyloctacosa-2,6,10,14,18,22,26-heptaen-1-yl)-3-methylnaphthalene-1,4-diyl dipropionate as a yellow oil.

$^1$H NMR (300 MHz, CDCl3) δ 7.76-7.55 (m, 2H), 7.55-7.33 (m, 2H), 5.09 (dt, J=5.4, 3.7, 7H), 3.39 (d, J=4.7, 2H), 2.77 (qd, J=7.6, 5.3, 4H), 2.22 (s, 3H), 2.15-1.82 (m, 24H), 1.76 (s, 3H), 1.67 (s, 3H), 1.58 (d, J=5.9, 18H), 1.37 (td, J=7.6, 6.1, 6H).

$^{13}$C NMR (75 MHz, CDCl3) δ 173.06, 172.64, 136.40, 135.38, 135.11, 131.45, 126.44, 126.35, 124.60, 124.44, 124.13, 121.56, 121.38, 77.65, 77.23, 76.81, 39.94, 39.80, 27.74, 27.21, 27.02-26.89, 26.80, 25.92, 17.90, 16.59, 16.24, 13.26, 9.63.

MS: m/z [M+Na]$^+$ calcd for C$_{52}$H$_{74}$O$_4$: 785.55; found: 785.7.

Example 8

To a solution of 2-((2E,6E,10E,14E,18E,22E)-3,7,11,15,19,23,27-heptamethyloctacosa-2,6,10,14,18,22,26-heptaen-1-yl)-3-methylnaphthalene-1,4-diyl dipropionate (5.59 g, 7.0 mmol) in a mixture of THF (100 mL) and H$_2$O (25 mL) LiOH.H$_2$O (2.35 g, 56 mmol) was added. The resulting solution was degassed in an ultrasonic bath for 5 min and stirred at 50° C. for 20 h after which 3 M HCl (aq) was added until pH 3. The resulting reaction mixture was extracted with EtOAc (2×250 mL). The organic layers were combined, dried (Na$_2$SO$_4$), filtrated and the solvent was removed under reduced pressure. The crude product was purified by flash chromatography (heptane:EtOAc gradient) to obtain 2.23 g (45%) of 2-((2E,6E,10E,14E,18E,22E)-3,7,11,15,19,23,27-heptamethyloctacosa-2,6,10,14,18,22,26-heptaen-1-yl)-4-hydroxy-3-methylnaphthalen-1-yl propionate (A) and 1.48 g (30%) of 3-((2E,6E,10E,14E,18E,22E)-3,7,11,15,19,23,27-heptamethyloctacosa-2,6,10,14,18,22,26-heptaen-1-yl)-4-hydroxy-2-methylnaphthalen-1-yl propionate (B).

MS: m/z [M+Na]$^+$ calcd for C$_{49}$H$_{70}$O$_3$: 729.52; found: 729.5.

NMR date of product A $^1$H NMR (400 MHz, CDCl$_3$) δ 8.07-8.01 (m, 1H), 7.61-7.56 (m, 1H), 7.44-7.38 (m, 2H), 5.15-4.98 (m, 8H), 3.43-3.28 (m, 2H), 2.80 (q, J=7.6, 2H), 2.27 (s, 3H), 2.14-1.88 (m, 24H), 1.76 (s, 3H), 1.66 (s, 3H), 1.61-1.52 (m, 18H), 1.36 (t, J=7.6, 3H).

NMR date of product B $^1$H NMR (400 MHz, CDCl$_3$) δ 8.10 (d, J=7.4, 1H), 7.60 (d, J=7.5, 1H), 7.45-7.36 (m, 2H), 5.28-5.20 (m, 1H), 5.17-4.99 (m, 7H), 3.51 (d, J=6.8, 2H), 2.76 (q, J=7.5, 2H), 2.23 (s, 3H), 2.18-1.90 (m, 24H), 1.85 (s, 3H), 1.66 (s, 3H), 1.63-1.48 (m, 18H), 1.38 (t, J=7.6, 3 H).

Example 9

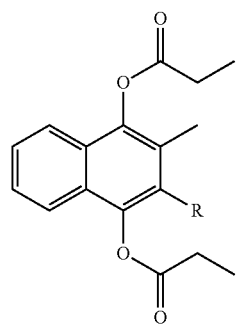

LiOH·H$_2$O, THF, H$_2$O, 50° C., 20 h
→

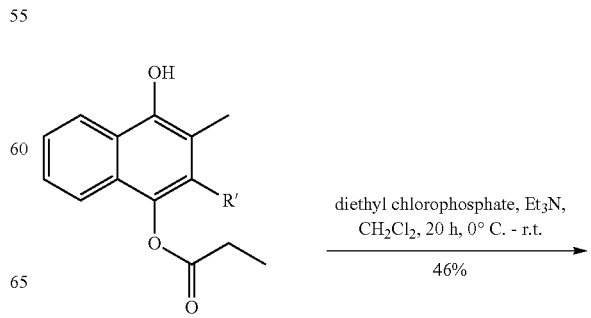

diethyl chlorophosphate, Et$_3$N, CH$_2$Cl$_2$, 20 h, 0° C. - r.t.
→
46%

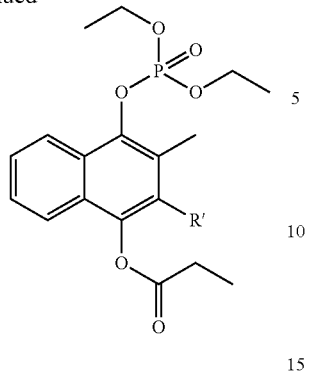

2-((2E,6E,10E,14E,18E,22E)-3,7,11,15,19,23,27-Heptamethyloctacosa-2,6,10,14,18,22,26-heptaen-1-yl)-4-hydroxy-3-methylnaphthalen-1-yl propionate (0.14 g, 0.20 mmol) was dissolved in $CH_2Cl_2$ (6 mL) and cooled to 0° C. To this solution diethyl chlorophosphate (43 μL, 0.30 mmol) and $Et_3N$ (42 μL, 0.30 mmol) were added and the reaction mixture was stirred at r.t. for 20 h after which the solvent was removed under reduced pressure. The crude product was purified by flash chromatography (heptane:EtOAc gradient) to obtain 50 mg (46%) of 4-((diethoxyphosphoryl)oxy)-2-((2E,6E,10E,14E,18E,22E)-3,7,11,15,19,23,27-heptamethyloctacosa-2,6,10,14,18,22,26-heptaen-1-yl)-3-methylnaphthalen-1-yl propionate as a yellow oil.

$^1H$ NMR (400 MHz, $CDCl_3$) δ 8.18 (d, J=8.2, 1H), 7.60 (d, J=8.0, 1H), 7.51-7.38 (m, 2H), 5.16-4.98 (m, 7H), 4.25-4.07 (m, 4H), 3.38 (s, 2H), 2.75 (q, J=7.5, 2H), 2.44 (s, 3H), 2.09-1.90 (m, 23H), 1.76 (s, 3H), 1.70-1.62 (m, 3H), 1.62-1.52 (m, 16H), 1.35 (t, J=7.5, 3H), 1.26 (t, J=7.0, 6 H) ppm;

$^{13}C$ NMR (101 MHz, $CDCl_3$) δ 173.04, 142.68, 141.91, 136.50, 135.41, 135.17, 135.14, 135.12, 135.10, 131.44, 130.80, 126.94, 126.90, 126.82, 126.79, 126.51, 126.50, 126.45, 126.16, 124.63, 124.50, 124.49, 124.41, 124.16, 122.94, 121.37, 121.12, 4.95, 64.89, 39.96, 39.94, 39.84, 32.10, 27.74, 27.30, 26.99, 26.95, 26.93, 26.89, 25.90, 22.90, 17.89, 16.62, 16.35, 16.28, 16.22, 16.21, 14.32, 14.01, 9.57 ppm.

MS: m/z $[M+H]^+$ calcd for $C_{53}H_{76}NO_6P$: 843.5693; found: 843.6.

N-Boc-Val-OH (67 mg, 0.32 mmol), DMAP (47 mg, 0.38 mmol) and DCC (78 mg, 0.38 mmol) were added to a solution of 2-((2E,6E,10E,14E,18E,22E)-3,7,11,15,19,23,27-heptamethyloctacosa-2,6,10,14,18,22,26-heptaen-1-yl)-4-hydroxy-3-methylnaphthalen-1-yl propionate (0.15 g, 0.21 mmol) in $CH_2Cl_2$ (5 mL). The reaction mixture was stirred at r.t. for 20 h after which the mixture was diluted with $Et_2O$ (20 mL). The organic solution was then washed with 5% citric acid (15 mL) and brine (10 mL), dried ($Na_2SO_4$), filtered and the solvent was removed under reduced pressure. The crude product was purified by flash chromatography (heptane:EtOAc gradient) to obtain 54 mg (28%) of 3-((2E,6E,10E,14E,18E,22E)-3,7,11,15,19,23,27-heptamethyloctacosa-2,6,10,14,18,22,26-heptaen-1-yl)-2-methyl-4-(propionyloxy)naphthalen-1-yl (tert-butoxycarbonyl)-L-valinate as a colourless oil.

$^1H$ NMR (400 MHz, $CDCl_3$) δ 7.73 (d, J=4.7, 1H), 7.60 (d, J=6.6, 1H), 7.47-7.39 (m, 2H), 5.15-4.99 (m, 8H), 4.76-4.62 (m, 1H), 3.44-3.29 (m, 2H), 2.76 (q, J=7.5, 2H), 2.60-2.48 (m, 1H), 2.23 (s, 3H), 2.11-1.90 (m, 24H), 1.75 (s, 3H), 1.67 (s, 3H), 1.62-1.52 (m, 18H), 1.47 (s, 9H), 1.36 (t, J=7.6, 3H), 1.18 (d, J=6.8, 3H), 1.10 (d, J=6.9, 3 H).

$^{13}C$ NMR (101 MHz, $CDCl_3$) δ 172.98, 170.99, 156.14, 142.70), 142.56, 136.51, 135.40, 135.16, 135.13, 135.11, 135.09, 131.43, 130.55, 127.18, 126.63, 126.51, 126.44, 126.39, 124.63, 124.49, 124.43, 124.16, 121.53, 121.32, 80.30, 59.13, 39.96, 39.94, 39.83, 31.14, 28.62, 28.55, 27.75, 27.23, 26.99, 26.95, 26.93, 26.89, 26.87, 25.90, 20.04, 17.89, 17.65, 16.61, 16.25, 16.22, 16.21, 13.47, 9.61.

MS: m/z $[M+Na]^+$ calcd for $C_{59}H_{87}NO_6$: 928.46; found: 928.7.

Example 10

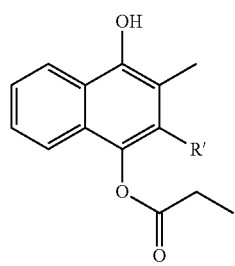

N-Boc-Val-OH, DMAP,
DCC, $CH_2Cl_2$, r.t., 20 h
⟶
28%

Example 11

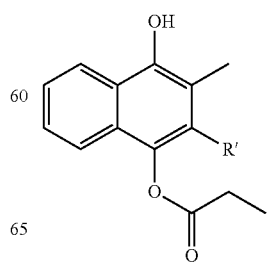

N-Boc-Gly-OH, DMAP,
DCC, $CH_2Cl_2$, r.t., 20 h
⟶
41%

27
-continued

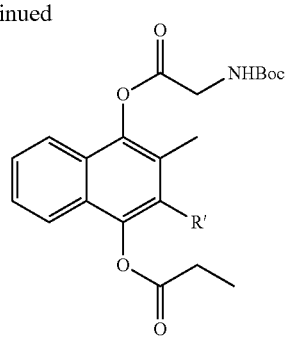

N-Boc-Gly-OH (55 mg, 0.26 mmol), DMAP (37 mg, 0.31 mmol) and DCC (64 mg, 0.31 mmol) were added to a solution of 2-((2E,6E,10E,14E,18E,22E)-3,7,11,15,19,23,27-heptamethyloctacosa-2,6,10,14,18,22,26-heptaen-1-yl)-4-hydroxy-3-methylnaphthalen-1-yl propionate (0.12 g, 0.17 mmol) in CH$_2$Cl$_2$ (5 mL). The reaction mixture was stirred at r.t. for 20 h after which the mixture was diluted with Et$_2$O (20 mL). The organic solution was then washed with 5% citric acid (15 mL) and brine (10 mL), dried (Na$_2$SO$_4$), filtered and the solvent was removed under reduced pressure. The crude product was purified by flash chromatography (heptane:EtOAc gradient) to obtain 60 mg (41%) of 4-(((tert-butoxycarbonyl)glycyl)oxy)-2-((2E,6E,10E,14E,18E,22E)-3,7,11,15,19,23,27-heptamethyloctacosa-2,6,10,14,18,22,26-heptaen-1-yl)-3-methylnaphthalen-1-yl propionate as a yellow solid.

$^1$H NMR (400 MHz, CDCl$_3$) δ 7.66-7.62 (m, 1H), 7.60-7.55 (m, 1H), 7.41-7.35 (m, 2H), 5.13-4.90 (m, 8H), 4.29 (d, J=5.1, 2H), 3.25 (s, 2H), 2.70 (q, J=7.6, 2H), 2.16 (s, 3H), 2.05-1.82 (m, 24H), 1.69 (s, 3H), 1.60 (s, 3H), 1.56-1.46 (m, 18H), 1.41 (s, 9H), 1.30 (t, J=7.6, 3 H).

$^{13}$C NMR (101 MHz, CDCl$_3$) δ 171.84, 168.33, 157.01, 142.77, 142.30, 142.30, 136.60, 136.37, 135.43, 135.18, 135.15, 135.13, 135.10, 131.51, 131.48, 130.60, 127.18, 126.69, 126.53, 126.31, 124.64, 124.50, 124.44, 124.17, 121.58, 121.26, 80.54, 39.95, 39.83, 28.54, 27.76, 27.21, 27.00, 26.94, 26.90, 26.87, 25.91, 17.90, 16.63, 16.26, 16.23, 13.34, 9.59.

MS: m/z [M+Na]$^+$ calcd for C$_{56}$H$_{81}$NO$_6$: 886.60; found: 886.8.

Example 12

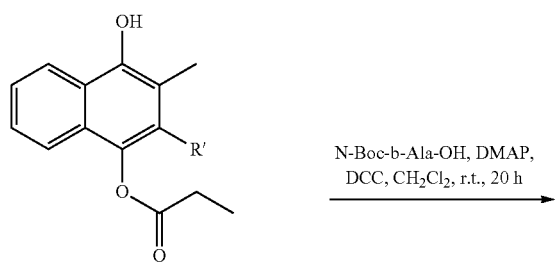

28
-continued

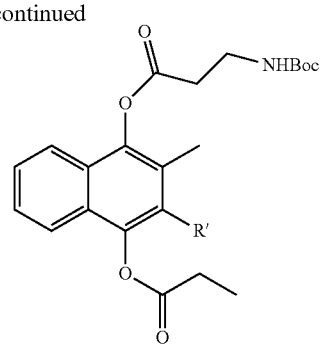

N-Boc-β-Ala-OH (57 mg, 0.30 mmol), DMAP (44 mg, 0.36 mmol) and DCC (74 mg, 0.36 mmol) were added to a solution of 2-((2E,6E,10E,14E,18E,22E)-3,7,11,15,19,23,27-heptamethyloctacosa-2,6,10,14,18,22,26-heptaen-1-yl)-4-hydroxy-3-methylnaphthalen-1-yl propionate (0.14 g, 0.20 mmol) in CH$_2$Cl$_2$ (10 mL). The reaction mixture was stirred at r.t. for 20 h. The resulting mixture was diluted with CH$_2$Cl$_2$ (25 mL), filtrated, washed with 5% citric acid (15 mL) and brine (10 mL), dried (Na$_2$SO$_4$), filtered and the solvent was removed under reduced pressure. The crude product was purified by flash chromatography (heptane:EtOAc gradient) to obtain 80 mg (34%) of 3-((2E,6E,10E,14E,18E,22E)-3,7,11,15,19,23,27-heptamethyloctacosa-2,6,10,14,18,22,26-heptaen-1-yl)-2-methyl-4-(propionyloxy)naphthalen-1-yl 3-((tert-butoxycarbonyl)amino)propanoate as a light yellow solid.

$^1$H NMR (400 MHz, CDCl$_3$) δ 7.67-7.61 (m, 2), 7.47-7.41 (m, 2), 5.16-5.00 (m, 8H), 3.61-3.52 (m, 2H), 3.39 (s, 2H), 3.06-2.95 (m, 2H), 2.76 (q, J=7.5, 2H), 2.21 (s, 3H), 2.10-1.89 (m, 24H), 1.75 (s, 3H), 1.66 (s, 3H), 1.61-1.54 (m, 18H), 1.46 (s, 9H), 1.36 (t, J=7.6, 3 H).

$^{13}$C NMR (101 MHz, CDCl$_3$) δ 172.81, 168.62, 157.34, 142.64, 142.53, 136.56, 135.43, 135.19, 135.16, 135.15, 135.11, 131.46, 130.82, 130.61, 127.10, 126.61, 126.52, 126.47, 126.39, 124.64, 124.51, 124.49, 124.44, 124.15, 121.75, 121.66, 121.30, 39.97, 39.95, 39.84, 28.64, 27.77, 27.23, 27.00, 26.96, 26.94, 26.91, 26.87, 25.91, 17.90, 16.62, 16.26, 16.24, 16.23, 13.36, 9.60.

MS: m/z [M+Na]$^+$ calcd for C$_{57}$H$_{83}$NO$_6$: 900.61; found: 900.6.

Example 13

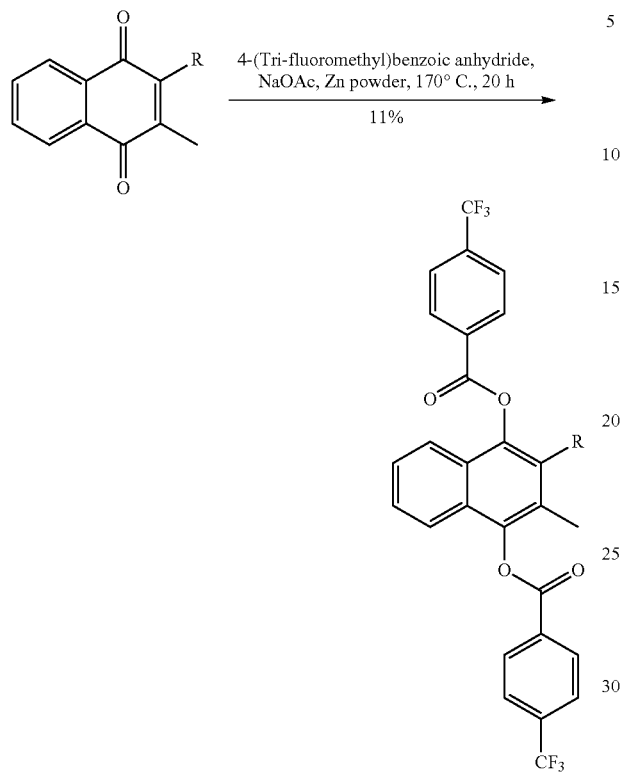

2-((2E,6E,10E,14E,18E,22E)-3,7,11,15,19,23,27-Heptamethyloctacosa-2,6,10,14,18,22,26-heptaen-1-yl)-3-methylnaphthalene-1,4-dione (0.524 g, 0.807 mmol), 4-(trifluoromethyl)benzoic anhydride (0.757 g, 2.09 mmol), NaOAc (87.3 mg, 1.06 mmol) and Zn powder (0.156 g, 2.38 mmol) were added together and heated to 170° C. After 23 h at 170° C. the reaction mixture was cooled down to r.t. and diluted with THF (40 mL). Et$_2$NH (20 mL) was added and the reaction mixture was stirred for another hour after which heptane (50 mL) was added. The resulting mixture was filtrated and the solvent of the filtrate was removed under reduced pressure. The crude product was purified by HPLC to obtain 83.7 mg (11%) of 2-((2E,6E,10E,14E,18E,22E)-3,7,11,15,19,23,27-heptamethyloctacosa-2,6,10,14,18,22,26-heptaen-1-yl)-3-methylnaphthalene-1,4-diyl bis(4-(trifluoromethyl)benzoate).

$^1$H NMR (400 MHz, CDCl$_3$) δ 8.45 (t, J=8.6, 4H), 7.88-7.81 (m, 4H), 7.76-7.65 (m, 2H), 7.45-7.40 (m, 2H), 5.17-4.98 (m, 7H), 3.59-3.34 (m, 2H), 2.31 (s, 3H), 2.15-1.83 (m, 24H), 1.65 (s, 3H), 1.62-1.46 (m, 18H), 1.24 (s, 3H).

MS: m/z [M+Na]$^+$ calcd for C$_{62}$H$_{72}$F$_6$O$_4$: 1017.52; found: 1017.3.

Example 14

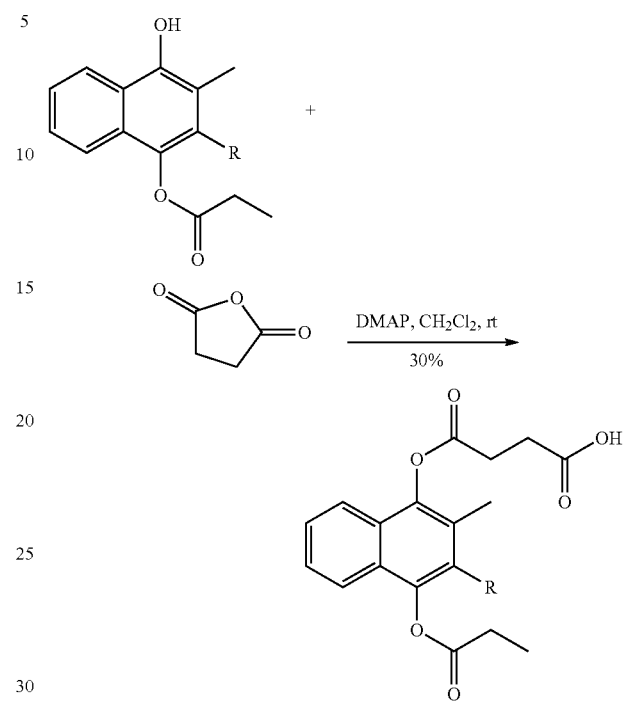

2-((2E,6E,10E,14E,18E,22E)-3,7,11,15,19,23,27-Heptamethyloctacosa-2,6,10,14,18,22,26-heptaen-1-yl)-4-hydroxy-3-methylnaphthalen-1-yl propionate (0.13 g, 0.18 mmol) was dissolved in CH$_2$Cl$_2$ (3 mL). To this solution succinic anhydride (37 mg, 0.37 mmol) and DMAP (45 mg, 0.37 mmol) were added and the reaction mixture was stirred at r.t. for 3.5 h after which the resulting solution was extracted with sat NaHCO$_3$ (aq). The aqueous phase was acidified with 2M HCl until pH 2 followed by extraction with EtOAc (2×100 mL). The combined organic phase was dried (Na$_2$SO$_4$), filtered and the solvent was removed under reduced pressure. The crude product was purified by flash chromatography using a gradient of EtOAc in heptane (see table 13) to obtain 43 mg (30%) of 4-((3-((2E,6E,10E,14E,18E,22E)-3,7,11,15,19,23,27-heptamethyloctacosa-2,6,10,14,18,22,26-heptaen-1-yl)-2-methyl-4-(propionyloxy)naphthalen-1-yl)oxy)-4-oxobutanoic acid as a yellow oil.

MS: m/z [M+Na]$^+$ calcd for C$_{53}$H$_{74}$NO$_6$: 829.54; found: 829.5.

$^1$H NMR (300 MHz, CDCl3) δ 7.75-7.68 (m, 1H), 7.64-7.57 (m, 1H), 7.46-7.38 (m, 2H), 5.15-4.97 (m, 8H), 3.45-3.30 (m, 2H), 3.10-3.00 (m, 2H), 2.90-2.81 (m, 2H), 2.80-2.68 (m, 2H), 2.21 (s, 3H), 2.12-1.85 (m, 23H), 1.74 (s, 3H), 1.66 (s, 4H), 1.61-1.49 (m, 18H), 1.35 (t, J=7.6, 3 H).

Example 15

2-((2E,6E,10E,14E,18E,22E)-3,7,11,15,19,23,27-heptamethyloctacosa-2,6,10,14,18,22,26-heptaen-1-yl)-3-methylnaphtalene-1,4-diyl dipropionate

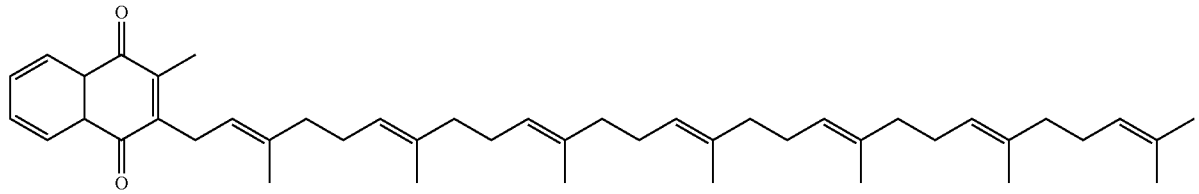

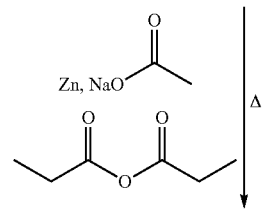

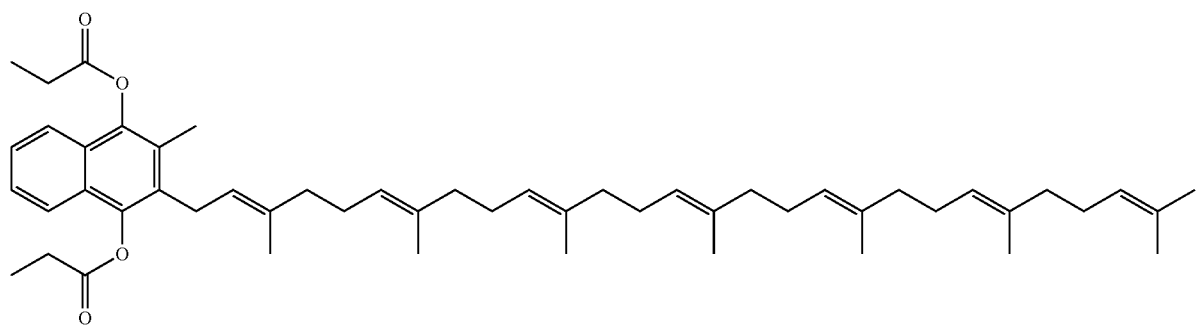

A mixture of Vitamin K2 MK-7 (MK: 3:94, 324 mg, 0.5 mmol), zinc dust (100 mg, 1.55 mmol), anhydrous sodium acetate (50 mg, 0.60 mmol) and propionic anhydride (7.5 ml, 80 mmol) was heated to 130° C. during 30 min., after cooling to room temperature poured into water (100 ml) and extracted with CHCl$_3$ (2×50 ml). The combined organic phase was dried (Na$_2$SO$_4$), filtered and concentrated. Excess propionic anhydride was distilled off under reduced pressure and the remaining oil purified by flash chromatography (heptane:EtOAc 95:5) to afford 250 mg yield of the title compound as a colorless solid.

$^1$H NMR (300 MHz, CDCl$_3$): δ 7.73-7.66 (2H, m), 7.49-7.46 (2H, m), 5.14-5.10 (7H, m), 3.44, 3.42, 2.83-2.77 (m, 4H), 2.26 (s, 3H), 2.24-1.95 (m, 24H), 1.80 (s, 3H), 1.71 (s, 3H), 1.63-1.60 (m, 18H), 1.43-1.40 (m, 6H).

$^{13}$C NMR (75 MHz, CDCl$_3$): δ 173.4, 172.6, 142.7, 136.60, 135.3, 131.7, 130.7, 127.3, 126.6, 124.7, 124.3, 121.6, 40.1, 27.9, 27.4, 27.1, 26.0, 18.0, 16.7, 16.4, 13.6, 9.9

Comparative Example

Acetic acid 3-(3,7,11,15,19,23,27-heptamethyl-octa-cosa-2,6,10,14,18,22,26-heptaenyl)-4-hydroxy-2-methyl-naphthalen-1-yl ester

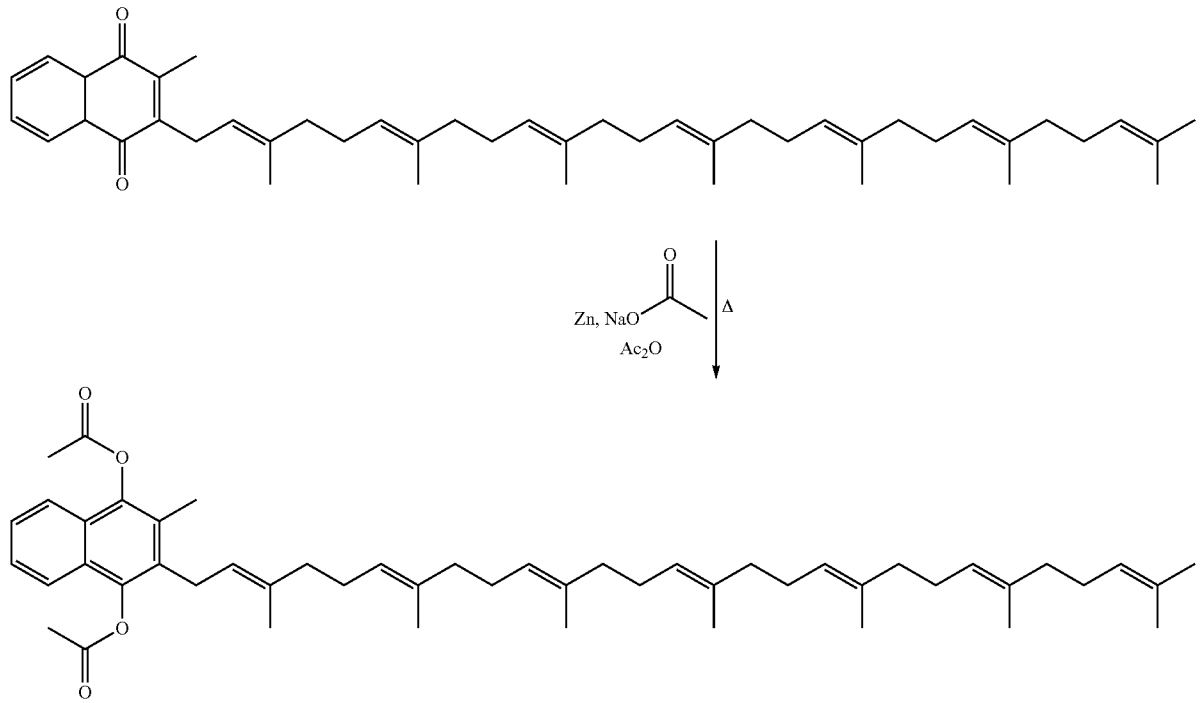

(Light was Off in the Hood During Reaction and Work-Up.)

A mixture of Vitamin K2 MK-7 (0.1997 g, 0.31 mmol), Zn (0.064 g, 0.98 mmol) and sodium acetate (0.0304 g, 0.37 mmol) in acetic acid anhydride (4.7 ml) was refluxed under N2-atmosphere for 30 minutes. The reaction mixture was cooled to room temperature, diluted with $CH_2Cl_2$ (50 ml), filtered, washed with water (20 ml) and brine (20 ml), dried ($Na_2SO_4$), and evaporated under reduced pressure to yield 0.160 g (71%) of the crude title compound as a colorless solid.

$^1$H NMR (300 MHz, $CDCl_3$) δ 7.60-7.78 (m, 2H), 7.38-7.53 (m, 2H), 4.90-5.24 (m, 7H), 3.43 (s, 2H), 2.49 (s, 3H), 2.47 (s, 3H), 2.25 (s, 3H), 1.85-2.16 (m, 24H), 1.79 (s, 3H), 1.69 (s, 3H), 1.59 (d, J=5.6 Hz, 18H).

$^{13}$C NMR (75 MHz, $CDCl_3$) δ 169.58, 169.15, 142.71, 142.42, 136.44, 135.34, 135.07, 135.06, 135.04, 135.02, 131.39, 130.46, 127.08, 126.48, 126.40, 126.38, 126.28, 124.53, 124.39, 124.34, 124.05, 121.52, 121.32, 121.22, 39.87, 39.75, 27.19, 26.90, 26.84, 26.81, 26.71, 25.85, 20.84, 20.77, 17.83, 16.53, 16.19, 16.16, 13.21.

MS (electrospray) (pos): 757/758/759 $(M+Na)^+$

Stability

The light stability of MK-7 was compared certain example compounds as hereinbefore described. Compounds were dissolved separately in ethyl acetate or MCT oil, transferred to glass vial (clear glass) and placed on the bench in a well lit laboratory (ordinary room lighting). The samples were analyzed after 19 hours of light exposure or more.

The samples were analyzed by HPLC using aHPLC_KB_001, with the HPLC conditions detailed below.

HPLC-DAD high pressure system: Agilent, LC system 1100 series
Analytical column: Supelcosil C-18, 4.6×250 mm, 5 µm
Column temperature: 40° C.
Flow rate: 1 mL/min
Injection volume: 8 µL
UV-detection: 270 nm/340 nm
Run time: 20 min
Eluent system: 50% Solvent C: MeOH/Water with 0.1% v/v acetic acid (95/5 v/v) 50% Solvent D: Isopropanol An overview of the results for the material tested is given in Table 1 and 2. The content of MK-7 and the MK-7 derivative in the samples have been quantified as % area of the total peak area in the chromatogram. The results shows that in MCT oil, MK-7 is sensitive to light in solution, as approximately 70% degradation is observed after 24 hours of light exposure. For the analogues of MK-7 the result is nearly unchanged after the 24 hours testing period, thus this compound is far more stable towards light exposure. In ethyl acetate MK-7 degrades even more rapidly. Note that Examples 1 and 7 are more stable than the diacetylated compound and that examples 2a and 2b show the synergistic behaviour discussed after table 2.

TABLE 1

In Ethyl acetate

| Material | Time point | |
|---|---|---|
| | Initial % | After 19 hrs % |
| MK-7 | 99.4 | 53.7 |
| Diacetylated MK-7 | 93.1 | 92.7 |
| Example 1 | 98.5 | 95.4 |
| Example 7 | 98.5 | 97.7 |
| Example 2a | 93.3 | 71.2 (23.4% MK-7) |
| Example 2b | 91.5 | 87.6 (2.8% MK-7) |

The results shows that MK-7 is sensitive to light in solution, as approximately 50% degradation is observed after 19 hours of light exposure.

TABLE 2 in MCT oil

| Compound | Start purity from CoA (%) | Purity after 1 h (%) | Purity after 1 d (%) | Purity after 3 d (%) |
|---|---|---|---|---|
| MK7 | 99 | 97.2 | 73.5 | 32.2 |
| Example 1 | 98.5 | 98.3 | 97.3 | 92.9 |
| Example 2A | 93.3 (+4% MK7) | 83.9 (+13.1% MK7) | 72.5 (+18.0% MK7) | 53.3 (+23.65 MK7) |
| Example 2B | 91.5 | 91.9 (+2.7% MK7) | 84.6 (+4.1% MK7) | 63.8 (+5.6% MK7) |
| Example 4 | 86.7 | 86.4 | 84.4 | 81.5 |
| Example 7 | 98.5 | 98.0 | 96.7 | 93.8 |
| Example 9 | 90.7 | 90.1 | 89.0 | 84.2 |
| Example 10 | 93.5 | 92.7 | 92.0 | 89.0 |
| Example 12 | 92 | 91.9 | 89.4 | 84.4 |
| Example 13 | 90.2 | 83.6 | 84.8 | 79.6 |

An interesting point to notice in this data is the degradation of Examples 2A and 2B. As we note, these degrade to give MK-7 and we note increasing levels of Mk-7 over time. What is surprising however is that the MK-7 which is formed is not itself then degrading rapidly. There appears to be a stabilisation of the MK-7 by the presence of the Example 2a and Example 2b products. The compounds act synergistically together therefore to aid stabilisation of the MK-7.

Example 3—In Vivo Testing

Brief Procedure: Mice

Male mice C57Bl6 with weights ranging from 38-45 grams were randomised and allocated to different groups with MK-7 compounds or derivatives. Groups had four mice in each group (except ex 2b when only 3 mice were tested). Prior to the experiment mice were allowed to eat regular chow ad libitum. On the day of the experiment, mice were administered MK-7 compounds and derivatives dissolved in ethanol, by oral gavage (2 mg/kg MK-7 equimolar; 100 ul/40 g mouse or MK-7 in corn oil 1 mg/kg). At the time of oral gavage, feed but not water was removed.

In venous blood was collected at four hours (300-500 ul) after oral feeding, and then mice were euthanized by cervical dislocation. Blood was collected in tubes coated with EDTA and immediately placed on ice prior to preparation of plasma.

Plasma was prepared by centrifugation at 10,000 g for 10 min, aliquoted and frozen to −20° C. until quantification of MK-7.

Brief Procedure: Rats:

Male Rats aged 6 to 8 weeks and weighing around 180 to 225 g. Animals were fasted overnight with free access to water. Animals were administered test substance by oral gavage with a dose of 100 μg/kg body weight (in recommended formulation and dose volume). Blood samples (150-200 μl) were collected at various time points during the next 48 hours post dose.

To determine the bioavailability of different formulations containing MK-7 in male e Sprague Dawley Rats through gavage. Formulations were both dissolved in sunflower oil. Approximately 0.4 ml/animal (depending on the weight of the animal) via oral gavage (100 μg/kg body weight). There were 6 animals per formulation. Blood samples were collected from the tail vein of each animal and transferred into lithium heparin tubes at 2 and 12 hours post dose. Quantification of analyte in plasma was determined by LC-MS-MS analysis: Analyte: MK-7 in plasma. The data are mean of four measurements (low and high values are not included).

TABLE 3

In mice

| | 4 hrs mean value uptake ng/ml MK-7 |
|---|---|
| MICE: 2 mg/kg dissolved in ethanol/water | |
| MK-7 | 4 |
| Example 12 | 2.5 |
| Example 2A | 1.9 |
| Example 2B | 4 |
| MICE: 1 mg/kg dissolved in corn oil | |
| MK-7 | 1.7 |
| Example 12 | 1.2 |

TABLE 4

RAT study 0.1 mg/kg in oil (sunflower oil)

| Compound | 2 hrs, ng/ml MK-7 | 12 hrs ng/ml MK-7 |
|---|---|---|
| MK-7 | 3.6 | 2.7 |
| Example 7 | 2.2 | 2.7 |

The serum level is the same in rats 12 hours after administration for both Ex 7 and MK-7. In mice Examples 12, 2A, 2B, dissolved in ethanol, all examples showed MK-7 in plasma after 4 hours. In mice Example 12, dissolved in corn oil, the agent was taken up and MK-7 measured in plasma after 4 hours.

In both experiments it is clear that the prodrugs give MK-7 in plasma.

The invention claimed is:

1. A method of treating osteoporosis, cancer, diabetes, male infertility or cardiovascular disease comprising administering to a patient in need thereof a compound of formula (I)

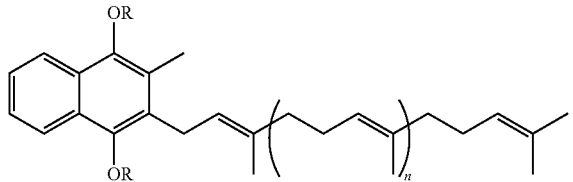

(I)

wherein each R is independently —COAr or —COC$_{1-6}$ alkyl group wherein both R groups are not COCH$_3$ simultaneously;

each R$^6$ is H or C1-6 alkyl;

each Ar is an optionally substituted phenyl or naphthyl group, said substitutent being a C1-6 alkyl, CHalH$_2$, CHal$_2$H, CHal$_3$, OH, OC1-6Alkyl, COOR$^6$;

and n is 3 to 8; or a salt or solvate thereof.

2. A method as claimed in claim 1 wherein both R groups are identical.

3. A method as claimed in claim 1 wherein one R is a —COC$_{2-6}$ alkyl group.

4. A method as claimed in claim 1 wherein said compound is

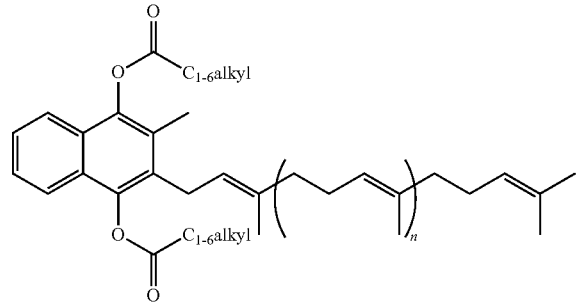

wherein n is 5.